US012766229B2

(12) United States Patent
Sivakumaran et al.

(10) Patent No.: US 12,766,229 B2
(45) Date of Patent: Oct. 20, 2026

(54) COATING COMPOSITIONS, POLYMERIC COATINGS, AND METHODS

(71) Applicant: COVALON TECHNOLOGIES, LTD., Mississauga (CA)

(72) Inventors: Daryl Sivakumaran, Hamilton (CA); Daryl Knight, Mississauga (CA); Vyacheslav Dudnyk, Mississauga (CA); Valerio DiTizio, North York (CA)

(73) Assignee: COVALON TECHNOLOGIES, LTD., Mississauga (CA)

(*) Notice: Subject to any disclaimer, the term of this patent is extended or adjusted under 35 U.S.C. 154(b) by 0 days.

(21) Appl. No.: 18/778,274

(22) Filed: Jul. 19, 2024

(65) Prior Publication Data

US 2024/0374794 A1 Nov. 14, 2024

Related U.S. Application Data

(62) Division of application No. 15/938,537, filed on Mar. 28, 2018, now Pat. No. 12,042,580.

(Continued)

(51) Int. Cl.
*A61L 33/00* (2006.01)
*A61L 33/06* (2006.01)

(Continued)

(52) U.S. Cl.
CPC ....... *A61L 33/0088* (2013.01); *A61L 33/0005* (2013.01); *A61L 33/0035* (2013.01);

(Continued)

(58) Field of Classification Search
CPC ...... A61L 31/088; A61L 31/16; C08F 297/04; B29C 45/1634
See application file for complete search history.

(56) References Cited

U.S. PATENT DOCUMENTS 5,380,790 A 1/1995 Chen et al.
8,877,256 B2 * 11/2014 Dudnik ................ A61L 31/088 514/495

(Continued)

FOREIGN PATENT DOCUMENTS

WO WO 2009/015476 A1 2/2009
WO WO 2011/038483 A1 4/2011
WO WO 2013/006947 A1 1/2013

OTHER PUBLICATIONS

Gratzl et al., Mechanistic approaches on the antibacterial activity of poly(acrylic acid) copolymers, Colloids and Surfaces B: Biointerfaces 126 (2015), pp. 98-105 (Year: 2015).*

(Continued)

*Primary Examiner* — Dah-Wei D. Yuan
*Assistant Examiner* — Andrew J Bowman
(74) *Attorney, Agent, or Firm* — Lathrop GPM LLP; Laura Labeots

(57) ABSTRACT

A coating composition comprises an aqueous solution comprising at least one vinyl carboxylic acid monomer and at least one neutral monomer, wherein the at least one neutral monomer has a glass transition temperature of less than about 100° C. in homopolymeric form. A device comprises a protonated polyacrylate coating, wherein the device is inherently antimicrobial, anti-thrombogenic, flexible, and/or sheds few to no particulates.

13 Claims, 7 Drawing Sheets

Related U.S. Application Data

(60) Provisional application No. 62/478,187, filed on Mar. 29, 2017.

(51) Int. Cl.
*C08F 220/06* (2006.01)
*C09D 4/00* (2006.01)
*C09D 5/14* (2006.01)
*C09D 133/10* (2006.01)

(52) U.S. Cl.
CPC ......... *A61L 33/0094* (2013.01); *A61L 33/064* (2013.01); *C08F 220/06* (2013.01); *C09D 4/00* (2013.01); *C09D 5/14* (2013.01); *C09D 133/10* (2013.01); *A61L 2300/404* (2013.01); *A61L 2300/42* (2013.01); *A61L 2300/608* (2013.01); *A61L 2400/10* (2013.01); *A61L 2420/02* (2013.01); *A61L 2420/08* (2013.01)

(56) References Cited

U.S. PATENT DOCUMENTS

| | | | |
|---|---|---|---|
| 2007/0104925 A1 | 5/2007 | Huber et al. |
| 2009/0035388 A1 | 2/2009 | Dudnik et al. |
| 2013/0039953 A1 | 2/2013 | Dudnyk et al. |
| 2014/0017335 A1 | 1/2014 | Dimov et al. |
| 2016/0166738 A1 | 6/2016 | Tramontano et al. |

OTHER PUBLICATIONS

Examination Report No. 1 for Australian Patent Application No. 2023236512, dated Jun. 27, 2025.
Examination Report No. 1 for Australian Patent Application No. 2018241528, dated Nov. 11, 2022.
Examination Report No. 2 for Australian Patent Application No. 2018241528, dated Sep. 27, 2023.
Extended European Search Report for European Patent Application No. 18776812.2, dated Nov. 9, 2020.
Gratzl et al, "Antimicrobial Activity of Poly (Acrylic Acid) Block Copolymers," Materials Science and Engineering C, May 1, 2014, 38: 94-100.
Gratzl et al., "Mechanistic approaches on the antibacterial activity of poly(acrylic acid) copolymers", Colloids Surf B Biointerfaces, Feb. 1, 2015, 126: 98-105, Epublished Dec. 15, 2014.
International Search Report and Written Opinion for PCT International Patent Application No. PCT/CA2018/050376, dated Jun. 8, 2018.
Mondal et al, "Acrylic Monomers Based Emulsion Copolymer for Coating Application," Indian Journal of Fibre & Textile Research, Jun. 2005, 30: 184-189.
Nho et al, "Graft Polymerization of Acrylic Acid and Methacrylic Acid onto Radiation- Peroxidized Polyethylene Film in Presence of Metallic Salt and Sulfuric Acid," Journal of Applied Polymer Science, Feb. 28, 1997, 63(9): 1101-1106.
Pillay et al, "A Review of Polymeric Refabrication Techniques to Modify Polymer Properties for Biomedical and Drug Delivery Applications," AAPS PharmSciTech, Jun. 2013, 14(2): 692-711, Epublished Mar. 30, 2013.
Polymer Database.com, "Polymer Chemistry, Copolymerization of Vinyl Polymers", revised Nov. 26, 2019, https://polymerdatabase.com/polymer%20chemistry/copolymers.html.
Sherazi et al., "Graft Polymerization", Encyclopedia of Membranes, Living Reference Work Entry, Dec. 26, 2015, pp. 1-2.
Tomić et al, "Smart Poly(2-hydroxyethyl methacrylate/itaconic acid) Hydrogels for Biomedical Application," Radiation Physics and Chemistry, 2010, 79(5): 643-649.

* cited by examiner

A

B

C

A

B

C

A

A

B

C

COATING COMPOSITIONS, POLYMERIC COATINGS, AND METHODS

FIELD

The present invention relates to coating compositions. More specifically, the present invention is, in aspects, concerned with coating compositions, polymeric coatings, and related methods of making and using same.

BACKGROUND

Modern medical devices are often composed of polymers that are generally well tolerated by the human body and for this reason, along with their flexibility and chemical stability, polymer-based medical devices are widely used in current clinical practice. The relative "bioinertness" of synthetic medical polymers is both a strength and a weakness in that given enough exposure to a polymer-based device, the host will eventually encapsulate the device with fibrous material since tissue integration with the device is not possible. Similarly, for devices within the bloodstream the generation of thrombus on the device can lead to severe complications. The inability of the host to recognize an implant as anything other than a foreign body is a drawback shared by polymeric devices regardless of their specific composition. One potential solution to the problem of polymer-host incompatibility is to change the surface properties of the polymer to allow for improved biocompatibility without sacrificing the beneficial bulk properties of the polymer. The ability to impart specific surface chemistries to polymeric medical devices also may contribute to the development of improved artificial organs, biosensors, and drug delivery systems.

One example of a surface modification employed to enhance the original properties of a medical device is the application of lubricious coatings, which are often used to improve access for delivery and placement of endovascular devices such as catheters. These hydrophilic coatings increase a device's lubricity, which reduces the frictional forces between the device and other devices or the vascular tissue itself. Historically, trade-offs came with improving the devices' lubricity through coating and maintaining the devices' mechanical integrity (i.e. minimizing particulate generation).

In a recent FDA Safety Communication on Lubricious Coating Separations[1], the FDA warns health care providers of the potential for hydrophilic coatings to separate (e.g. peel, flake, shed, delaminate, slough off) from medical devices and present an embolic risk to the patient. Since Jan. 1, 2014, the FDA has received approximately 500 Medical Device Reports (MDRs) describing separation of hydrophilic and/or hydrophobic coatings on medical devices such as guidewires, catheters, and introducers that have been used for cerebrovascular, cardiovascular and peripheral vascular procedures. Serious adverse events reported in these MDRS and in the scientific literature include pulmonary embolism, pulmonary infarction, myocardial embolism, myocardial infarction, embolic stroke, tissue necrosis and death. To date the FDA has not set an acceptable threshold of particulates generated from medical devices, but has specified recommendations for quantifying particulate size and count using an appropriate simulated-use model.[2, 3, 4, 5]

[1] FDA, Safety, Intravascular Medical Devices: FDA Safety Communications—Lubricious Coating Separation, Posted Nov. 23, 2015, http://www.fda-.gov/Safety/MedWatch/SafetyInformation/SafetyAlertsfor HumanMedical-Products/ucm473924.htm

[2] FDA, Regulatory Information, Guidance for Industry and FDA Staff—Non-Clinical Engineering Tests and Recommended Labeling for Intravascular Stents and Associated Delivery Systems, Posted Apr. 18, 2010, http://www.fda.gov/RegulatoryInformation/Guidances/ucm071863.htm

[3] FDA, Regulatory Information, Select Updates for Non-Clinical Engineering Tests and Recommended Labeling for Intravascular Stents and Associated Delivery Systems, Posted Aug. 30, 2013, http://www.fda.gov/downloads/MedicalDevices/DeviceRegulationandGuidance/GuidanceDocuments/UCM458490.pdf

[4] Association for the Advancement of Medical Instrumentation (AAMI) Technical Information Report (TIRA2:2010), Evaluation of Particulates associated with vascular medical devices.

[5] ASTM International, Standard Guide for Coating Inspection and Acute Particulate Characterization of Coating Drug-Eluting Vascular Stent Systems, Published November 2011. DOI: 10.1520/F2743-11.

It has been found that many other coating technologies that cite low particulate generation, however, have significantly higher particulate counts in comparison to the uncoated device alone.[6]

[6] Babcock D E, Hergenrother R W, Craig D A, Kolodgie F D, Virmani R. In vivo distribution of particulate matter from coated angioplasty balloon catheters, Biomaterials, 2013, 34, 3196-205.

In previous work shown in U.S. Pat. Nos. 6,808,738 and 8,840,927, stable polyacrylate coatings were made by the free radical polymerization of a monomer selected from the group consisting of acrylic acid, methacrylic acid, 2-carboxyethyl acrylate, 4-vinylbenzoic acid, itaconic acid, and mixtures thereof. The coating was ionized in an aqueous base to render the coating lubricious and was then saturated with cations from a salt such as sodium lactate to prepare the coating for loading with a silver-based antimicrobial agent. In U.S. Pat. No. 8,697,112, a method for treating a surface with a therapeutic agent is disclosed. The method comprises precipitating a therapeutic agent from a hydrophilic polymeric base layer with which the therapeutic agent has been complexed, to form a layer comprising microparticles of the therapeutic agent on the hydrophilic polymeric base layer, the hydrophilic polymeric base layer being grafted to the surface.

U.S. Pat. No. 5,278,200 describes biocompatible heparin-like material and surfaces thereof are made by co-polymerization of acrylic acid (AA) and 2-acrylamido-2-methyl propane sulfonic acid (AMPS) and attaching the copolymer to a suitable substrate or blending the copolymer into a suitable substrate. The material produced also possesses surface slip-properties and some decreased bacterial and platelet adherence.

U.S. Pat. Nos. 6,087,415, 6,534,559, and 6,838,491 describe biomedical devices with stable, hydrophilic and antimicrobial coatings. The coatings are formed using a coupling agent to bond a carboxyl containing hydrophilic coating to the surface by ester or amide linkages.

U.S. Pat. No. 6,403,113 describes anti-microbic copolymers and derivatives thereof that are used in methods for controlling odor in hygienic articles. The copolymers comprise at least two different ethylenically unsaturated monomers.

U.S. Pat. No. 6,468,649 describes an implantable medical device having a substrate with a hydrophilic coating composition to limit in vivo colonization of bacteria and fungi. The hydrophilic coating composition includes a hydrophilic polymer with a molecular weight in the range from about 100,000 to about 15 million selected from copolymers of acrylic acid, methacrylic acid, isocrotonic acid and combinations thereof.

U.S. Patent Application Publication No. 2010/0210725 describes a method for grafting a copolymer onto a polyolefin substrate including the following steps: (a) irradiating the substrate with ionizing radiation to obtain an activated polyolefin substrate, (b) bringing into contact the activated polyolefin substrate with a mixture of at least two compounds in distilled water including: (i) from 10 to 40% by volume, related to the total volume of the reaction medium, of a hydrophilic unsaturated monomer selected from monomers having the formula $CH_2R_1R_2$, wherein $R_1$ is H or methyl, $R_2$ is —COOH, —$NH_2$, —$CON(R_3)_2$, and $R_3$ is H or methyl, (ii) from 20 to 50% by volume, related to the total volume of the reaction medium, of an antimicrobial agent having an average molecular weight of at least 200 $g \cdot mol^{-1}$, to thereby form a copolymer-grafted polyolefin substrate.

U.S. Patent Application Publication No. 2011/0171158 describes a polymeric material that has a plurality of different pendant groups that include a first pendant group containing a —COOH group or a salt thereof, a second pendant group containing a poly (alkylene oxide) group, a third pendant group containing a silicon-containing group, and a fourth pendant group containing a quaternary amino group. The polymeric material can be used, for example, to provide coatings that can be antifouling, antimicrobial, or both.

Gratzl et al. (Materials Science and Engineering C 38 (2014) 94-100) describe that poly(acrylic acid) (PAA) containing diblock copolymers can kill bacteria and prevent biofilm formation. The PAA diblock copolymers with poly (styrene) and poly(methyl methacrylate) were synthesized via anionic polymerization of tert-butyl acrylate with styrene or methyl methacrylate and subsequent acid-catalyzed hydrolysis of the tert-butyl ester. The copolymers were characterized via nuclear magnetic resonance spectroscopy (NMR), size-exclusion chromatography (SEC), Fourier transform infrared spectroscopy (FTIR), elemental analysis, and acid-base titrations. Copolymer films with a variety of acrylic acid contents were produced by solvent casting, characterized by atomic force microscopy (AFM) and tested for their antimicrobial activity against *Staphylococcus aureus, Escherichia coli*, and *Pseudomonas aeruginosa*. The antimicrobial activity of the acidic diblock copolymers increased with increasing acrylic acid content, independent of the copolymer-partner, the chain length and the nanostructure.

Gratzl et al. (Colloids and Surfaces B: Biointerfaces 126 (2015) 98-105) used poly(styrene)-poly(acrylic acid)-diblock copolymers (PS-b-PAA) to describe the major variables causing the material to have a bactericidal effect on *Escherichia coli* ATCC 25922 in aqueous suspensions. Upon contact with water, the surface structure of the copolymer changes, the pH value decreases, and the PAA-block migrates toward the surface. Systematically modified antimicrobial tests show that the presence of acid-form PAA provides maximum antimicrobial activity of the material in slightly acidic conditions, and that an ion-exchange effect is the most probable mechanism. Antimicrobially inactive counter-ions inhibit the bactericidal activity of the copolymers, but the material can be regenerated by treatment with acids.

There is a need for alternative compositions to overcome or mitigate at least some of the deficiencies of the prior art, or to provide a useful alternative.

SUMMARY

In accordance with an aspect, there is provided a coating composition comprising an aqueous solution comprising at least one vinyl carboxylic acid monomer and at least one neutral monomer, wherein the at least one neutral monomer has a glass transition temperature of less than about 100° C. in homopolymeric form.

In an aspect, the vinyl carboxylic acid monomer is a compound of formula (I):

Formula I

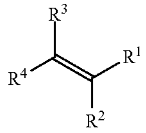

and/or a salt, hydrate, solvate, tautomer, optical isomer, or combination thereof;

wherein $R^1$ is —COOH or —$R^5$—COOH, wherein $R^5$ is selected from a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group; and wherein $R^2$, $R^3$, and $R^4$ are each independently selected from H, a halide, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group.

In an aspect, the vinyl carboxylic acid monomer is selected from the group consisting of acrylic acid, 2-bromoacrylic acid, 2-(bromomethyl) acrylic acid, 2-carboxyethyl acrylate, 2-ethylacrylic acid, itaconic acid, methacrylic acid, 2-propylacrylic acid, sodium acrylate, sodium methacrylate, 2-(trifluoromethyl) acrylic acid, 4-vinylbenzoic acid, and combinations thereof.

In an aspect, the neutral monomer is a compound of formula (II):

Formula II

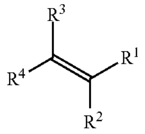

and/or a hydrate, solvate, tautomer, optical isomer, or combination thereof;

wherein $R^1$ is —$C(O)R^5$ or —$R^6(O)R^5$ wherein $R^5$ and $R^6$ are independently selected from a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group; and wherein $R^2$, $R^3$, and $R^4$ are each independently selected from H, a halide, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group.

In an aspect, the neutral monomer is selected from the group consisting of acrylates, methacrylates, acrylamides, methacrylamides, vinyl compounds, and combinations thereof.

In an aspect, the neutral monomer is selected from the group consisting of methyl acrylate, methyl methacrylate, and combinations thereof.

In an aspect, the neutral monomer has a glass transition temperature of less than about 90° C., 80° C., 70° C., 60° C., 50° C., 40° C., 30° C., 20° C., or 10° C. in homopolymeric form.

In an aspect, a copolymer formed from the polymerization of the at least one vinyl carboxylic acid monomer and the at least one neutral monomer has a glass transition temperature that is lower than about 100° C.

In an aspect, the composition comprises the vinyl carboxylic acid monomer in an amount of from about 20% to about 90% by weight.

In an aspect, the composition comprises the neutral monomer in an amount of from about 10% to about 80% by weight.

In accordance with an aspect, there is provided a polymeric coating comprising a copolymer graft-polymerized from at least one water soluble vinyl carboxylic acid monomer and at least one water soluble neutral monomer, wherein the at least one water soluble neutral monomer has a glass transition temperature of less than about 100° C. in homopolymeric form.

In an aspect, the vinyl carboxylic acid monomer is a compound of formula (I):

Formula I

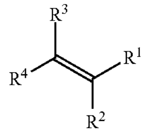

and/or a salt, hydrate, solvate, tautomer, optical isomer, or combination thereof;

wherein $R^1$ is —COOH or —$R^5$—COOH, wherein $R^5$ is selected from a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group; and wherein $R^2$, $R^3$, and $R^4$ are each independently selected from H, a halide, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group.

In an aspect, the vinyl carboxylic acid monomer is selected from the group consisting of acrylic acid, 2-bromoacrylic acid, 2-(bromomethyl) acrylic acid, 2-carboxyethyl acrylate, 2-ethylacrylic acid, itaconic acid, methacrylic acid, 2-propylacrylic acid, sodium acrylate, sodium methacrylate, 2-(trifluoromethyl) acrylic acid, 4-vinylbenzoic acid, and combinations thereof.

In an aspect, the neutral monomer is a compound of formula (II):

Formula II

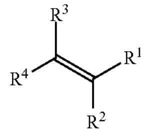

and/or a hydrate, solvate, tautomer, optical isomer, or combination thereof;

wherein $R^1$ is —C(O)$R^5$ or —$R^6$(O)$R^5$ wherein $R^5$ and $R^6$ are independently selected from a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group; and wherein $R^2$, $R^3$, and $R^4$ are each independently selected from H, a halide, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group.

In an aspect, the neutral monomer is selected from the group consisting of acrylates, methacrylates, acrylamides, methacrylamides, vinyl compounds, and combinations thereof.

In an aspect, the neutral monomer is selected from the group consisting of methyl acrylate, methyl methacrylate, and combinations thereof.

In an aspect, the neutral monomer has a glass transition temperature of less than about 90° C., 80° C., 70° C., 60° C., 50° C., 40° C., 30° C., 20° C., or 10° C. in homopolymeric form.

In an aspect, a copolymer formed from the polymerization of the at least one vinyl carboxylic acid monomer and the at least one neutral monomer has a glass transition temperature that is lower than about 100° C.

In an aspect, the vinyl carboxylic acid monomer is protonated.

In an aspect, the composition comprises the vinyl carboxylic acid monomer in an amount of from about 20% to about 90% by weight.

In an aspect, the composition comprises the neutral monomer in an amount of from about 10% to about 80% by weight.

In an aspect, the coating is inherently antimicrobial, optionally showing a greater than about 2-log reduction in microbes within about 24 hours, such as a greater than about 2-log, 3-log, 4-log, or 5-log reduction in microbes within about 5 minutes, 30 minutes, 1 hour, 2 hours, 6 hours, 12 hours, 18 hours, or 24 hours.

In an aspect, the coating is inherently antithrombogenic, optionally showing a greater than about 80% reduction, such as a greater than about 85%, 90%, 95%, 96%, 97%, 98%, or 99% reduction, relative to an uncoated surface.

In an aspect, the coating releases low or no particulates, optionally releasing fewer particulates than an uncoated surface.

In an aspect, the coating is lubricious.

In an aspect, the coating has high resistance to cracking when expanded or inflated.

In an aspect, the coating has high resistance to delamination as demonstrated by the maintenance of hydrophilicity after exposure to high shear force.

In an aspect, exposure of the polymeric coating to an altered pH environment restores its inherent biological activity, such as antimicrobial activity, antithrombogenicity, low to no particulate release, lubricity, resistance to cracking, and/or maintenance of hydrophilicity.

In an aspect, the coating further comprises an antimicrobial agent.

In an aspect, the antimicrobial agent is selected from the group consisting of chlorhexidine, octenidine, benzalkonium chloride, benzethonium chloride, polyhexamethylene biguanide, copper, zinc, silver, chlorine, fluoroquinolones, b-lactams, macrolides, aminoglycosides, tetracyclines, and combinations thereof.

In an aspect, the antimicrobial agent comprises silver ions.

In an aspect, the silver ions are derived from a silver salt selected from the group consisting of silver phosphate, silver citrate silver lactate, silver acetate, silver benzoate, silver chloride, silver carbonate, silver iodide, silver iodate, silver nitrate, silver laurate, silver sulfadiazine, silver palmitate, and mixtures thereof.

In accordance with an aspect, there is provided a medical device comprising a coating made from the coating composition described herein or comprising the polymeric composition described herein.

In an aspect, the medical device is made from a material selected from the group consisting of polyurethanes, polyamides, polyesters, polycarbonates, polyureas, polyethers, polyorganosiloxanes, polysulfones, polytetrafluoroethylene, polysiloxanes, and combinations thereof.

In an aspect, the medical device is selected from the group consisting of dressings, sutures, scaffolds, fracture fixation devices, catheters, stents, implants, tubings, rods, prostheses, electrodes, endoscopes, cardiac valves, pacemakers, dental implants, and surgical, medical or dental instruments.

In accordance with an aspect, there is provided a method of coating a device, the method comprising:

applying at least one vinyl carboxylic acid monomer to the device;

applying at least one neutral monomer to the device, wherein the at least one water soluble neutral monomer has a glass transition temperature of less than about 100° C. in homopolymeric form; and graft-polymerizing the at least one vinyl carboxylic acid monomer and the at least one neutral monomer onto the device.

In an aspect, the vinyl carboxylic acid monomer is a compound of formula (I):

Formula I

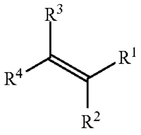

and/or a salt, hydrate, solvate, tautomer, optical isomer, or combination thereof;

wherein $R^1$ is —COOH or —$R^5$—COOH, wherein $R^5$ is selected from a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group; and wherein $R^2$, $R^3$, and $R^4$ are each independently selected from H, a halide, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group.

In an aspect, the vinyl carboxylic acid monomer is selected from the group consisting of acrylic acid, 2-bromoacrylic acid, 2-(bromomethyl) acrylic acid, 2-carboxyethyl acrylate, 2-ethylacrylic acid, itaconic acid, methacrylic acid, 2-propylacrylic acid, sodium acrylate, sodium methacrylate, 2-(trifluoromethyl) acrylic acid, 4-vinylbenzoic acid, and combinations thereof.

In an aspect, the neutral monomer is a compound of formula (II):

Formula II

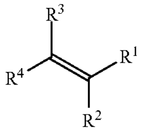

and/or a hydrate, solvate, tautomer, optical isomer, or combination thereof;

wherein $R^1$ is —C(O)$R^5$ or —$R^6$(O)$R^5$ wherein $R^5$ and $R^6$ are independently selected from a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group; and wherein $R^2$, $R^3$, and $R^4$ are each independently selected from H, a halide, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group.

In an aspect, the neutral monomer is selected from the group consisting of acrylates, methacrylates, acrylamides, methacrylamides, vinyl compounds, and combinations thereof.

In an aspect, the neutral monomer is selected from the group consisting of methyl acrylate, methyl methacrylate, and combinations thereof.

In an aspect, the neutral monomer has a glass transition temperature of less than about 90° C., 80° C., 70° C., 60° C., 50° C., 40° C., 30° C., 20° C., or 10° C. in homopolymeric form.

In an aspect, a copolymer formed from the polymerization of the at least one vinyl carboxylic acid monomer and the at least one neutral monomer has a glass transition temperature that is lower than about 100° C.

In an aspect, the composition comprises the vinyl carboxylic acid monomer in an amount of from about 20% to about 90% by weight.

In an aspect, the composition comprises the non-ionic monomer in an amount of from about 10% to about 80% by weight.

In an aspect, the method further comprises ionizing the coating after the polymerizing step.

In an aspect, ionizing the coating comprises applying a basic solution to the coating.

In an aspect, the basic solution has a pH of greater than about 8.0.

In an aspect, the basic solution is selected from the group consisting of TRIZMA base, disodium tetraborate, sodium carbonate, and hydroxides such as ammonium hydroxide, calcium hydroxide, sodium hydroxide, and mixtures thereof.

In an aspect, ionizing the coating comprises soaking the device in the basic solution for a time of from about 1 minute to about 30 minutes, such as about 6 minutes.

In an aspect, the method further comprises applying an antimicrobial agent to the coating after the step of ionizing the coating.

In an aspect, the step of applying the antimicrobial agent comprises soaking the device in a solution comprising the antimicrobial agent for a time of from about 1 to about 30 minutes, such as from about 3 to about 5 minutes.

In an aspect, the antimicrobial agent is selected from the group consisting of chlorhexidine, octenidine, benzalkonium chloride, benzethonium chloride, polyhexamethylene biguanide, copper, zinc, silver, chlorine, fluoroquinolones, b-lactams, macrolides, aminoglycosides, tetracyclines, and combinations thereof.

In an aspect, the antimicrobial agent comprises silver ions.

In an aspect, the silver ions are derived from a silver salt selected from the group consisting of silver phosphate, silver citrate, silver lactate, silver acetate, silver benzoate, silver chloride, silver carbonate, silver iodide, silver iodate, silver nitrate, silver laurate, silver sulfadiazine, silver palmitate, and mixtures thereof In an aspect, the method further comprises applying a photostabilizer such as brilliant green and/or pyrrolidone carboxylic acid to the device.

In an aspect, the device is soaked in a solution comprising the photostabilizer, pyrrolidone carboxylic acid, and silver ions.

In an aspect, the method further comprises washing the device in a basic solution after the step of applying the antimicrobial agent.

In an aspect, the method further comprises protonating the coating after the polymerizing step.

In an aspect, wherein protonating the coating comprises applying an acidic solution to the coating.

In an aspect, the acidic solution has a pH of less than about 7.0, such as less than about 6.5, less than about 6.0, less than about 5.5, less than about 5.0, less than about 4.5, or less than about 4.0, or from about 4.0 to about 7.0, such as from about 5.0 to about 6.5, such as from about 5.0 to about 6.0.

In an aspect, the acidic solution comprises an acid selected from the group consisting of HCl, HBr, HI, $HClO_4$, $H_2SO_4$, $HNO_3$, sodium hydrogen sulfate, sulfonic acid, acetic acid, phosphoric acid, phosphorous acid, sulfurous acid, trichloroacetic acid, salicylic acid, phthalic acid, nitrous acid, lactic acid, hydroiodic acid, formic acid, citric acid, tartaric acid, and combinations thereof.

In an aspect, the acidic solution comprises HCl.

In an aspect, the step of applying the acidic solution to the coating for a time of from about 1 to about 30 minutes, such as about 6 minutes.

In an aspect, the method further comprises a preliminary step of applying an initiator solution to the device.

In an aspect, the initiator solution is a photoinitiator solution.

In an aspect, the photoinitiator solution comprises a photoinitiator selected from the group consisting of peresters, α-hydroxyketones, benzil ketals, benzoins and their derivatives and mixtures thereof, such as tert-butylperbenzoate and/or benzophenone.

In an aspect, the step of applying an initiator solution to the device comprises soaking the device in the initiator solution for a time of from about 1 minute to about 30 minutes, such as about 6 minutes.

In an aspect, the polymerizing step comprises applying UV light to the device.

In an aspect, UV light is applied to the device for approximately 6 minutes.

In an aspect, the polymerizing step further comprises bubbling an inert gas such as nitrogen through the monomers, before and/or during the step of applying UV light to the device.

In an aspect, the polymerizing step comprises soaking the device in the vinyl carboxylic acid monomers and the neutral monomers for a time of from about 1 to about 30 minutes, such as about 6 minutes.

In an aspect, the vinyl carboxylic acid monomers and the neutral monomers are present in the same solution.

In an aspect, the method further comprises a step of washing the device in ethanol immediately after the step of polymerizing for a time of from about 1 minute to about 30 minutes, such as about 6 minutes.

In an aspect, the method further comprises a final step of washing the device in deionized water for a time of from about 1 minute to about 30 minutes, such as about 6 to about 10 minutes.

In an aspect, the method further comprises air drying the device.

In an aspect, the method further comprises sterilizing the device.

In an aspect, the coating is inherently antimicrobial, optionally showing a greater than about 2-log reduction in microbes within about 24 hours, such as a greater than about 2-log, 3-log, 4-log, or 5-log reduction in microbes within about 5 minutes, 30 minutes, 1 hour, 2 hours, 6 hours, 12 hours, 18 hours, or 24 hours.

In an aspect, the coating is inherently antithrombogenic, optionally showing a greater than about 80% reduction, such as a greater than about 85%, 90%, 95%, 96%, 97%, 98%, or 99% reduction, relative to an uncoated surface.

In an aspect, the coating releases low or no particulates, optionally releasing fewer particulates than an uncoated surface.

In an aspect, the coating is lubricious.

In an aspect, the coating has high resistance to cracking when expanded or inflated.

In an aspect, the coating has high resistance to delamination as demonstrated by the maintenance of hydrophilicity after exposure to high shear force.

In an aspect, exposure of the polymeric coating to an altered pH environment restores its inherent biological activity, such as antimicrobial activity, antithrombogenicity, low to no particulate release, lubricity, resistance to cracking, and/or maintenance of hydrophilicity.

In an aspect, the device is made from a material selected from the group consisting of polyurethanes, polyamides, polyesters, polycarbonates, polyureas, polyethers, polyorganosiloxanes, polysulfones, polytetrafluoroethylene, polysiloxanes, and combinations thereof.

In an aspect, the device is a medical device selected from the group consisting of dressings, sutures, scaffolds, fracture fixation devices, catheters, stents, implants, tubings, rods, prostheses, electrodes, endoscopes, cardiac valves, pacemakers, dental implants, and surgical, medical or dental instruments.

In accordance with an aspect, there is provided a device made by the method described herein.

In accordance with an aspect, there is provided a device comprising a protonated polyacrylate coating, wherein the device is inherently antimicrobial, anti-thrombogenic, flexible and/or sheds few to no particulates.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION

Figure 1:
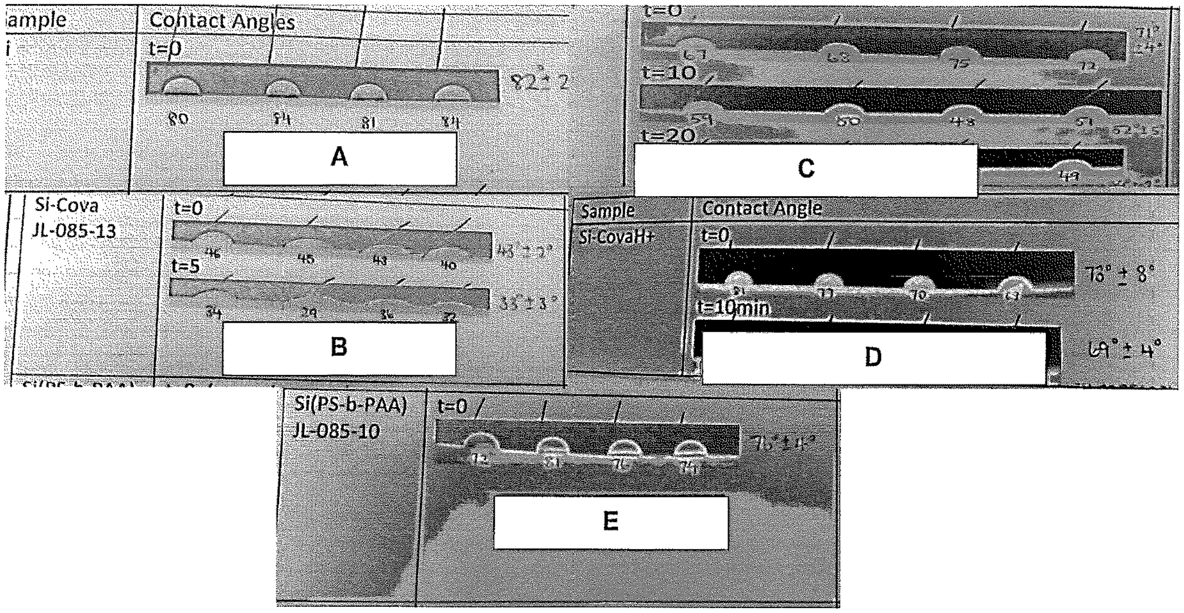
FIG. 1 shows the contact angle of A) Silicone; B) Comparative Coating (I); C) Non-Eluting Antimicrobial Coating; D) Non-Eluting Antimicrobial Coating (1 base wash); and E) Comparative Coating (II).

Described herein, in aspects, are hybrid synthetic biomaterials. These biomaterials provide functional interpenetrating covalent coating compositions that have improved integration between the coating and substrate. In view of this, and at least in part due to the methods by which they are made, the biomaterials described herein have beneficial properties as will be described below.

Definitions

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

The compounds described herein may have asymmetric centers, chiral axes, and chiral planes (as described, for example, in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers, with all possible isomers and mixtures thereof, including optical isomers, E isomers, and Z isomers. In addition, the compounds disclosed herein may exist as tautomers and both tautomeric forms are intended to be encompassed herein, even though only one tautomeric structure may be depicted.

Generally, reference to a certain element such as hydrogen or H is meant to, if appropriate, include all isotopes of that element.

Where the term "alkyl group" is used, either alone or within other terms such as "haloalkyl group" and "alkylamino group", it encompasses linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In embodiments, alkenyl groups are "lower alkenyl" groups having two to about four carbon atoms. Examples of alkenyl groups include, but are not limited thereto, ethenyl, propenyl, allyl, propenyl, butenyl and 4-methylbutenyl. The terms "alkenyl group" and "lower alkenyl group", encompass groups having "cis" and "trans" orientations, or alternatively, "E" and "Z" orientations.

The term "alkynyl group" denotes linear or branched carbon radicals having at least one carbon-carbon triple bond. The term "alkynyl group" can encompass conjugated and non-conjugated carbon-carbon triple bonds or combinations thereof. Alkynyl group, for example and without being limited thereto, can encompass two to about twenty carbon atoms or, in a particular embodiment, two to about twelve carbon atoms. In embodiments, alkynyl groups are "lower alkynyl" groups having two to about ten carbon atoms. Some examples are lower alkynyl groups having two to about four carbon atoms. Examples of such groups include propargyl, butynyl, and the like.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six carbon atoms and one or more hydroxyl groups. Examples of such groups include hydroxymethyl, hydroxyethyl, hydroxypropyl, hydroxybutyl and hydroxyhexyl.

The term "alkoxy group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups. In other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroatom" means an atom other than carbon. Typically, heteroatoms are selected from the group consisting of sulfur, phosphorous, nitrogen and oxygen atoms. Groups containing more than one heteroatom may contain different heteroatoms.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two rings typically have 8 to 12 member atoms, more typically 8 to 10 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The term "carbocyclic group" means a saturated or unsaturated carbocyclic hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups may contain 4 to 10 carbon atoms, typically 4 to 7 carbon atoms, and more typically 5 to 6 carbon atoms in the ring. Bicyclic carbocyclic groups may contain 8 to 12 carbon atoms, typically 9 to 10 carbon atoms in the rings.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heterocyclic groups can be fused, spiro, or bridged ring systems. Monocyclic heterocyclic groups may contain 4 to 10 member atoms (i.e., including both carbon atoms and at least 1 heteroatom), typically 4 to 7, and more typically 5 to 6 in the ring. Bicyclic heterocyclic groups may contain 8 to 18 member atoms, typically 9 or 10 member atoms in the rings. Representative heterocyclic groups include, by way of example, pyrrolidine, imidazolidine, pyrazolidine, piperidine, 1,4-dioxane, morpholine, thiomorpholine, piperazine, 3-pyrroline and the like.

The term "heterogeneous group" means a saturated or unsaturated chain of non-hydrogen member atoms comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

When the term "unsaturated" is used in conjunction with any group, the group may be fully unsaturated or partially unsaturated. However, when the term "unsaturated" is used in conjunction with a specific group defined herein, the term maintains the limitations of that specific group. For example, an unsaturated "carbocyclic group", based on the limitations of the "carbocyclic group" as defined herein, does not encompass an aromatic group.

The terms "carboxy group" or "carboxyl group", whether used alone or with other terms, such as "carboxyalkyl group", denotes —(C═O)—O—.

The term "carbonyl group", whether used alone or with other terms, such as "aminocarbonyl group", denotes —(C═O)—.

The terms "alkylcarbonyl group" denotes carbonyl groups which have been substituted with an alkyl group. In certain embodiments, "lower alkylcarbonyl group" has lower alkyl group as described above attached to a carbonyl group.

The term "aminoalkyl group" encompasses linear or branched alkyl groups having one to about ten carbon atoms any one of which may be substituted with one or more amino groups. In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N, N-dimethyl-aminoethyl, N, N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "arylalkenyl group" encompasses aryl-substituted alkenyl groups. In embodiments, the arylalkenyl groups are "lower arylalkenyl" groups having aryl groups attached to alkenyl groups having two to six carbon atoms. Examples of such groups include phenylethenyl. The aryl in said arylalkenyl may be additionally substituted with halo, alkyl, alkoxy, haloalkyl and haloalkoxy.

The term "arylalkynyl group" encompasses aryl-substituted alkynyl groups. In embodiments, arylalkynyl groups are "lower arylalkynyl" groups having aryl groups attached to alkynyl groups having two to six carbon atoms. Examples of such groups include phenylethynyl. The aryl in said aralkyl may be additionally substituted with halo, alkyl, alkoxy, haloalkyl and haloalkoxy. The terms benzyl and phenylmethyl are interchangeable.

The term "alkylthio group" encompasses groups containing a linear or branched alkyl group, of one to ten carbon atoms, attached to a divalent sulfur atom. In certain embodiments, the lower alkylthio groups have one to three carbon atoms. An example of "alkylthio" is methylthio, ($CH_3S$—).

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "arylamino group" denotes amino groups which have been substituted with one or two aryl groups, such as N-phenylamino. The "arylamino" groups may be further substituted on the aryl ring portion of the group.

The term "heteroarylamino" denotes amino groups which have been substituted with one or two heteroaryl groups, such as N-thienylamino. The "heteroarylamino" groups may be further substituted on the heteroaryl ring portion of the group.

The term "aralkylamino group" denotes amino groups which have been substituted with one or two aralkyl groups. In other embodiments, there are phenyl-$C_1$-$C_3$-alkylamino groups, such as N-benzylamino. The "aralkylamino" groups may be further substituted on the aryl ring portion of the group.

The term "alkylaminoalkylamino group" denotes alkylamino groups which have been substituted with one or two alkylamino groups. In embodiments, there are $C_1$-$C_3$-alkylamino-$C_1$-$C_3$-alkylamino groups.

The term "arylthio group" encompasses aryl groups of six to ten carbon atoms, attached to a divalent sulfur atom. An example of "arylthio" is phenylthio. The term "aralkylthio group" encompasses aralkyl groups as described above, attached to a divalent sulfur atom. In certain embodiments there are phenyl-$C_1$-$C_3$-alkylthio groups. An example of "aralkylthio" is benzylthio.

The term "aryloxy group" encompasses optionally substituted aryl groups, as defined above, attached to an oxygen atom. Examples of such groups include phenoxy.

The term "aralkoxy group" encompasses oxy-containing aralkyl groups attached through an oxygen atom to other groups. In certain embodiments, aralkoxy groups are "lower aralkoxy" groups having optionally substituted phenyl groups attached to lower alkoxy group as described above.

The term "cycloalkyl group" includes saturated carbocyclic groups. In certain embodiments, cycloalkyl groups include $C_3$-$C_6$ rings. In embodiments, there are compounds that include, cyclopentyl, cyclopropyl, and cyclohexyl.

The term "cycloalkenyl group" includes carbocyclic groups that have one or more carbon-carbon double bonds; conjugated or non-conjugated, or a combination thereof. "Cycloalkenyl" and "cycloalkyldienyl" compounds are included in the term "cycloalkenyl". In certain embodiments, cycloalkenyl groups include $C_3$-$C_6$ rings. Examples include cyclopentenyl, cyclopentadienyl, cyclohexenyl and cycloheptadienyl. The "cycloalkenyl" group may have 1 to 3 substituents such as lower alkyl, hydroxyl, halo, haloalkyl, nitro, cyano, alkoxy, lower alkylamino, and the like.

The term "suitable substituent", "substituent" or "substituted" used in conjunction with the groups described herein refers to a chemically and pharmaceutically acceptable group, i.e., a moiety that does not negate the activity of the compounds described herein. It is understood that substituents and substitution patterns on the compounds described herein may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C═O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "fused" means in which two or more carbons/member atoms are common to two adjoining rings, e.g., the rings are "fused rings".

The pharmaceutically acceptable salts of the compounds described herein include the conventional non-toxic salts of the compounds as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds described herein can be synthesized from compounds containing a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Included herein are pharmaceutically acceptable salts, solvates and prodrugs of the compounds described and mixtures thereof.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," (or vice versa) wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effects described herein. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded by way of proviso or negative limitation, such as any specific compounds or method steps, whether implicitly or explicitly defined herein.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Coating Compositions

Described herein are coating compositions comprising at least one vinyl carboxylic acid monomer and at least one neutral monomer. Typically, the vinyl carboxylic acid monomer is a compound of formula (I):

Formula I

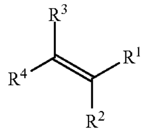

and/or a salt, hydrate, solvate, tautomer, optical isomer, or combination thereof. In Formula I, $R^1$ is typically —COOH or —$R^5$—COOH, wherein $R^5$ is selected from a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group.

In addition, $R^2$, $R^3$, and $R^4$ are typically each independently selected from H, a halide, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group.

In more specific aspects, $R^2$ is H, Br, or an alkyl group having from 1 to 3, 1 to 4, 1 to 5, 1 to 6, 1 to 7, 1 to 8, 1 to 9, or 1 to 10 carbon atoms, such as a methyl, ethyl, or propyl group, and the alkyl group may or may not comprise one or more halides, such as Br or F.

$R^3$ and $R^4$ are more typically each H.

$R^5$ is typically a substituted or unsubstituted aromatic group, such as a benzyl group, or $R^5$ is typically a substituted or unsubstituted hydrocarbon comprising one or more heteroatoms, such as O.

When present as a salt, for example, the vinyl carboxylic acid monomer is typically a sodium salt.

Specific non-limiting examples of the vinyl carboxylic acid monomer include acrylic acid, 2-bromoacrylic acid, 2-(bromomethyl) acrylic acid, 2-carboxyethyl acrylate, 2-ethylacrylic acid, itaconic acid, methacrylic acid, 2-propylacrylic acid, sodium acrylate, sodium methacrylate, 2-(trifluoromethyl) acrylic acid, 4-vinylbenzoic acid, and combinations thereof. Typically, the vinyl carboxylic acid comprises or consists of acrylic acid.

Typically, the neutral monomer is a compound of formula (II):

Formula II

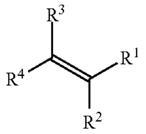

and/or a hydrate, solvate, tautomer, optical isomer, or combination thereof. In Formula II, $R^1$ is typically —C(O)$R^5$ or —$R^6$(O)$R^5$ wherein $R^5$ and $R^6$ are independently selected from a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group.

In more specific aspects, $R^2$ is H, Br, or an alkyl group having from 1 to 3, 1 to 4, 1 to 5, 1 to 6, 1 to 7, 1 to 8, 1 to 9, or 1 to 10 carbon atoms, such as a methyl, ethyl, or propyl group, and the alkyl group may or may not comprise one or more halides, such as Br or F.

$R^3$ and $R^4$ are more typically each H.

$R^5$ is typically an alkyl group having from 1 to 3, 1 to 4, 1 to 5, 1 to 6, 1 to 7, 1 to 8, 1 to 9, or 1 to 10 carbon atoms, such as a methyl, ethyl, or propyl group.

$R^6$ is typically a substituted or unsubstituted aromatic group, such as a benzyl group, or $R^6$ is typically a substituted or unsubstituted hydrocarbon comprising one or more heteroatoms, such as O.

When present as a salt, for example, the vinyl carboxylic acid monomer is typically a sodium salt.

In addition, $R^2$, $R^3$, and $R^4$ are typically each independently selected from H, a halide, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, and a substituted or unsubstituted heteroaromatic group.

Specific non-limiting examples of the neutral monomer include acrylates, methacrylates, acrylamides, methacrylamides, vinyl compounds, and combinations thereof, such as methyl acrylate, methyl methacrylate, and combinations thereof. Typically, the neutral monomer comprises or consists of methyl acrylate.

In particular aspects, the at least one neutral monomer has a glass transition temperature ($T_g$) of less than that of a homopolymer of acrylic acid (about 105° C.), when in homopolymeric form. It has been found that specifically choosing a neutral monomer with a $T_g$ of less than a homopolymer of acrylic acid, such as less than about 105° C. or, more typically less than about 100° C., "softens" the mechanical properties of the coating (relative to a pure polyacrylic acid homopolymer, for example) allowing for some expansion, such as in Foley catheter balloon inflation, with low to no cracking and/or delamination. Thus, copolymers made using the neutral monomers described herein with a homopolymeric $T_g$ below that of polyacrylic acid possess sufficient flexibility to allow for expansion of inflatable materials with minimal or no cracking or delamination.

In certain aspects, therefore, the at least one neutral monomer has a glass transition temperature that is less about 105° C. or, in more specific aspects, of less than about 100° C., 90° C., 80° C., 70° C., 60° C., 50° C., 40° C., 30° C., 20° C., or 10° C. in homopolymeric form.

In this way, a copolymer formed from the polymerization of the at least one vinyl carboxylic acid monomer and the at least one neutral monomer typically has a glass transition temperature that is lower than about 100° C., such as less than about 90° C., 80° C., 70° C., 60° C., 50° C., 40° C., 30° C., 20° C., or 10° C.

It will be understood that the vinyl carboxylic acid monomer may be present in the coating composition and/or the polymeric coating in any amount, typically from about 20% to about 90% by weight, such as from about 20%, 25%, 30%, 35%, 40%, 45%, 50%, 55%, 60%, 70%, or 75% to about 25%, 30%, 35%, 40%, 45%, 50%, 55%, 60%, 70%, 75%, or 80% by weight.

Likewise, the neutral monomer may be present in the coating composition and/or the polymeric coating in any amount, typically from about 10% to about 80% by weight, such as from about 10%, 15%, 20%, 25%, 30%, 35%, 40%, 45%, 50%, 55%, 60%, 70%, or 75% to about 15%, 20%, 25%, 30%, 35%, 40%, 45%, 50%, 55%, 60%, 70%, 75%, or 80% by weight.

The vinyl carboxylic acid and the neutral monomer may be present in the coating composition is various ratios, such as from about 1:50 to about 50:1, such as from about 1:50, 1:40, 1:30, 1:20, 1:10, 1:9, 1:8, 1:7, 1:6, 1:5, 1:4, 1:3, 1:2, or 1:1 to 2:1, 3:1, 4:1, 5:1, 6:1, 7:1, 8:1, 9:1, 10:1, 20:1, 30:1, 40:1, or 50:1.

The compositions may comprise additional excipients as would be understood to a skilled person.

Polymeric Coatings

The compositions described above are typically used to form polymeric coatings. The polymeric coatings comprise a copolymer graft-polymerized from at least one water soluble vinyl carboxylic acid monomer, as described above, and at least one water soluble neutral monomer, as described above.

In particular aspects, the vinyl carboxylic acid monomer is protonated in the polymeric coating. This is typically accomplished by soaking the polymeric coating in an acidic solution. It has been found that protonating the vinyl carboxylic acid monomer provides a coating that is inherently antimicrobial, optionally showing a greater than about 2-log reduction in microbes within about 24 hours, such as a greater than about 2-log, 3-log, 4-log, or 5-log reduction in microbes within about 5 minutes, 30 minutes, 1 hour, 2 hours, 6 hours, 12 hours, 18 hours, or 24 hours.

In alternative or additional aspects, the polymeric coating is inherently antithrombogenic, optionally showing a greater than about 80% reduction, such as a greater than about 85%, 90%, 95%, 96%, 97%, 98%, or 99% reduction, relative to an uncoated surface.

In further alternative or additional aspects, the polymeric coating releases low or no particulates, optionally releasing fewer particulates than an uncoated surface; the polymeric coating is lubricious; the polymeric coating has high resistance to cracking when expanded or inflated; and/or the polymeric coating has high resistance to delamination as demonstrated by the maintenance of hydrophilicity after exposure to high shear force. In aspects, one or more of these features are improved as compared to a polyacrylate (AA) coating.

In certain aspects, exposure of the polymeric coating to an altered pH environment, such as an acidic or basic environment, typically an acidic environment to reprotonate the surface, restores its inherent biological activity, such as antimicrobial activity, antithrombogenicity, low to no particulate release, lubricity, resistance to cracking, and/or maintenance of hydrophilicity. In aspects, one or more of these features are improved as compared to a polyacrylate (AA) coating.

The polymeric coating may comprise additional components, such as an additional therapeutic agent. The therapeutic agent in aspects is an antimicrobial agent, including one or more antibacterial agents, and/or one or more antifungal agents, and/or one or more antiviral agents, and/or one or more antiseptic agents, and/or combinations thereof.

In typical aspects, the antimicrobial agent is an antibacterial agent. While any antibacterial agent as described herein may be used in the polymeric coatings described herein, some non-limiting exemplary antibacterial agent include those classified as aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipo-peptide antibiotics, metal salts, as well as pharmacologically acceptable sodium salts, pharmacologically acceptable calcium salts, pharmacologically acceptable potassium salts, lipid formulations, derivatives and/or analogs of the above.

In other aspects, the antimicrobial agent includes an antifungal agent. Some exemplary classes of antifungal agents include imidazoles or triazoles such as clotrimazole, miconazole, ketoconazole, econazole, butoconazole, omoconazole, oxiconazole, terconazole, itraconazole, fluconazole, voriconazole (UK 109,496), posaconazole, ravuconazole or flutrimazole; the polyene antifungals such as amphotericin B, liposomal amphoterecin B, natamycin, nystatin and nystatin lipid formulations; the cell wall active cyclic lipopeptide antifungals, including the echinocandins such as caspofungin, micafungin, anidulfungin, cilofungin; LY121019; LY303366; the allylamine group of antifungals such as terbinafine. Yet other non-limiting examples of antifungal agents include naftifine, tolnaftate, mediocidin, candicidin, trichomycin, hamycin, aurefungin, ascosin, ayfattin, azacolutin, trichomycin, levorin, heptamycin, candimycin, griseofulvin, BF-796, MTCH 24, BTG-137586, pradimicins (MNS 18184), benanomicin; ambisome; nikkomycin Z; flucytosine, or perimycin.

In still other aspects, the antimicrobial includes an antiviral agent. Non-limiting examples of antiviral agents include cidofovir, amantadine, rimantadine, acyclovir, gancyclovir, pencyclovir, famciclovir, foscarnet, ribavirin, or valcyclovir. In some aspects the antimicrobial agent is an innate immune peptide or proteins. Some exemplary classes of innate peptides or proteins are transferrins, lactoferrins, defensins, phospholipases, lysozyme, cathelicidins, serprocidins, bacteriocidal permeability increasing proteins, amphipathic alpha helical peptides, and other synthetic antimicrobial amino acids, peptides, or proteins.

In other aspects, the polymeric coatings described herein may comprise at least one anticoagulant such as heparin, hirudin, EGTA, EDTA, urokinase, streptokinase, or hydrogen peroxide etc.

In typical aspects, the comprises an antimicrobial agent selected from the group consisting of chlorhexidine, octenidine, benzalkonium chloride, benzethonium chloride, polyhexamethylene biguanide, copper, zinc, silver, chlorine, fluoroquinolones, b-lactams, macrolides, aminoglycosides, tetracyclines, and combinations thereof.

More typically, the antimicrobial agent comprises silver ions, which are typically derived from a silver salt selected from the group consisting of silver phosphate, silver citrate silver lactate, silver acetate, silver benzoate, silver chloride, silver carbonate, silver iodide, silver iodate, silver nitrate, silver laurate, silver sulfadiazine, silver palmitate, and mixtures thereof.

The polymeric coatings may comprise additional agents and/or excipients as will be understood to a skilled person. For example, when silver ions are chosen as the antimicrobial agent, a dye and/or complexed silver, such as a photostabilizer (e.g., Brilliant Green) and/or pyrrolidone carboxylic acid, may be applied to the device, as is described in U.S. Pat. No. 8,877,256, which is incorporated herein by reference in its entirety.

The polymeric coatings described herein are typically graft-polymerized onto the surface of a medical device. The medical device is itself typically polymeric and is made from a material such as polyurethanes, polyamides, polyesters, polycarbonates, polyureas, polyethers, polyorganosiloxanes, polysulfones, polytetrafluoroethylene, polysiloxanes, or combinations thereof.

While non-limiting, the medical device is typically a device for use internally or for external use on wounds, for example. Thus, in particular aspects, the medical device is selected from the group consisting of dressings, sutures, scaffolds, fracture fixation devices, catheters, stents, implants, tubings, rods, prostheses, electrodes, endoscopes, cardiac valves, pacemakers, dental implants, and surgical, medical or dental instruments.

Methods of Coating

Described herein are methods of coating a device, such as a polymeric medical device. The method comprises applying at least one vinyl carboxylic acid monomer, as described above, to the device; applying at least one neutral monomer, as described above, to the device; and graft-polymerizing the at least one vinyl carboxylic acid monomer and the at least one neutral monomer onto the device.

Typically, after polymerizing the coating, the coating is washed with alcohol, such as ethanol, for a short period of time, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. In typical aspects, the device comprising the coating is soaked in ethanol, with or without agitation, for about 6 minutes.

After the alcohol wash, the coating is typically ionized by applying a basic solution to the coating. The basic solution typically has a pH of greater than about 7.0, 7.5, 8.0, 8.5, or 9.0. The basic solution may be any known basic solution but is typically selected from the group consisting of TRIZMA base, disodium tetraborate, sodium carbonate, and hydroxides such as ammonium hydroxide, calcium hydroxide, sodium hydroxide, and mixtures thereof, for example.

In typical aspects, ionizing the coating comprises soaking the device in the basic solution for a time of from about 1 minute to about 30 minutes, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. In typical aspects, the device comprising the coating is soaked in the basic solution with or without agitation for about 6 minutes.

Once the coating is ionized, an antimicrobial agent as described above may be applied to the coating typically by soaking the device in a solution comprising the antimicrobial agent for a time of from about 1 to about 30 minutes, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. Typically, the device comprising the ionized coating is soaked in a solution comprising the antimicrobial agent with or without agitation for a time of from about 3 to about 5 minutes.

When the chosen antimicrobial agent comprises silver ions, typically the method further comprises applying a dye and/or complexed silver, such as a photostabilizer and/or pyrrolidone carboxylic acid, to the device, as has been explained above. In this case, the dye and/or complexed silver, such as a photostabilizer (e.g., Brilliant Green) and/or pyrrolidone carboxylic acid, may be separately applied to the device or in combination, or in further combination with the silver ions. Typically, these agents are applied by soaking the device in a solution comprising the agents with or without agitation for a period of time such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes.

After the antimicrobial agent is applied to the device, the device is typically washed in a basic solution having a pH of greater than about 7.0, 7.5, 8.0, 8.5, or 9.0. The basic solution may be any known basic solution but is typically selected from the group consisting of TRIZMA base, disodium tetraborate, sodium carbonate, and hydroxides such as ammonium hydroxide, calcium hydroxide, sodium hydroxide, and mixtures thereof, for example.

In other aspects, after washing the device in ethanol, the method comprises protonating the coating. The coating is typically protonated by applying an acidic solution to the coating, wherein the acidic solution has a pH of less than about 7.0, such as less than about 6.5, less than about 6.0, less than about 5.5, less than about 5.0, less than about 4.5, or less than about 4.0, or from about 4.0 to about 7.0, such as from about 5.0 to about 6.5, such as from about 5.0 to about 6.0.

The acidic solution may be any known acidic solution, however, specific examples include acidic solutions comprising an acid selected from the group consisting of HCl, HBr, HI, $HClO_4$, $H_2SO_4$, $HNO_3$, sodium hydrogen sulfate, sulfonic acid, acetic acid, phosphoric acid, phosphorous acid, sulfurous acid, trichloroacetic acid, salicylic acid, phthalic acid, nitrous acid, lactic acid, hydroiodic acid, formic acid, citric acid, tartaric acid, and combinations thereof. Typically, the acidic solution comprises HCl.

The acidic solution may be applied to the coating for any period of time but typically, the device comprising the coating is soaked in the acidic solution for a time of from about 1 minute to about 30 minutes, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. In typical aspects, the device comprising the coating is soaked in the acidic solution with or without agitation for about 6 minutes.

Once the coating is protonated, an antimicrobial agent may further be added to the coating by soaking the device comprising the coating in a solution comprising the antimicrobial agent as explained above. In this way, the device will be inherently antimicrobial but will also elute an antimicrobial agent.

Prior to the polymerizing step, the method typically comprises a preliminary step of applying an initiator solution to the device. The initiator solution is typically a photoinitiator solution comprising a photoinitiator such as peresters, α-hydroxyketones, benzil ketals, benzoins and their derivatives and mixtures thereof, such as tert-butylperbenzoate and/or benzophenone.

The photoinitiator solution is typically applied to the device by soaking the device in the initiator solution for a time of from for a time of from about 1 minute to about 30 minutes, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. In typical aspects, the device is soaked in the photoinitiator solution with or without agitation for about 6 minutes. This results in a photoinitiator-coated device, which is typically placed into the monomer solution immediately after having been coated with the photoinitiator, such as without first drying the device.

Typically, the coating is then polymerized onto the device by applying UV light to the photoinitiator-coated device for a time of from about 1 minute to about 30 minutes, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. In typical aspects, the UV light is applied to the device for about 6 minutes with or without agitation, while the device is submerged in the vinyl carboxylic acid monomers and the neutral monomers solution.

The polymerizing step typically includes bubbling an inert gas such as nitrogen through the monomers, before and/or during the step of applying UV light to the device. Typically, the vinyl carboxylic acid monomers and the neutral monomers are present in the same solution, however, it is contemplated that the device could be soaked in the photoinitiator solution, followed by one monomer solution and then the other, whereafter polymerization is effected.

As noted above, the device is typically washed in ethanol after polymerization for a short period of time. This wash can assist in removing residual photoinitiator from the device and coating.

After the polymerization, protonation, and ionization steps are complete, and after any desired agents such as antimicrobial agents have been added to the coated device, the device is typically washed in deionized water for a time of from about 1 to about 30 minutes, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. Typically, the device comprising is soaked in deionized water, with or without agitation, for a time of from about 6 to about 10 minutes.

After the wash in deionized water, the coated device is typically air dried and is optionally sterilized and packaged.

The method described above may be fully manual, fully automated, or partially automated. In particular aspects, the method is carried out using the system described in International Patent Application Publication No. WO 2011/038483, which is incorporated herein by reference in its entirety.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1—Method of Making a Silver-Eluting Antimicrobial Coating

A polymeric base material, such as a silicone catheter, was coated with a silver-eluting antimicrobial coating as follows:

1. The device was soaked in an initiator ethanol solution (generally comprising tert-butylperbenzoate and benzophenone), for approximately 6 minutes.
2. The device was then soaked (without a prior drying step) in an aqueous monomer solution comprising acrylic acid and methyl acrylate for approximately 6 minutes with nitrogen purging.
3. UV initiated polymerization was conducted for about 6 minutes without removing the device from the aqueous monomer solution.
4. The device was washed in ethanol to remove excess photoinitiator for about 6 minutes.
5. The device was ionized/deprotonated to make a negatively charged lubricous surface using TRIZMA base solution for 6 minutes.
6. The device was then soaked in a silver solution (specifically silver acetate) with a photostabilizer (brilliant green) and pyrrolidone carboxylic acid in water for about 3-5 minutes.
7. The device was washed in TRIZMA base for about 10 minutes.
8. The device was washed in deionized water for about 10 minutes.
9. The device was air dried.

Example 2—Method of Making a Non-Eluting Antimicrobial Coating

A polymeric base material, such as a silicone catheter, was coated with a non-eluting antimicrobial coating as follows:

1. The device was soaked in an initiator ethanol solution (generally comprising tert-butylperbenzoate and benzophenone), for approximately 6 minutes.
2. The device was then soaked (without a prior drying step) in an aqueous monomer solution comprising acrylic acid and methyl acrylate for approximately 6 minutes with nitrogen purging.
3. UV initiated polymerization was conducted for about 6 minutes without removing the device from the aqueous monomer solution.
4. The device was washed in ethanol to remove excess photoinitiator for about 6 minutes.
5. The device was washed in HCl (pH about 3.4-4) for about 6 minutes to make a protonated surface.
6. The device was washed in deionized water for about 6 minutes.
7. The device was air dried.

Example 3—Testing Non-Eluting Antimicrobial Coating

Introduction

These experiments were conducted to characterize the coating properties, especially as compared to similar commercially available polymers. In particular, these experiments quantify coating features such as hydrophilicity, abrasion resistance, and antimicrobial regeneration ability.

Materials and Methods

Coating of the non-eluting antimicrobial silicone sheets was completed as follows:

1. Silicone sheets of about 12"×2" were washed and soaked in ethanol for 6 minutes.
2. The silicone sheets were then soaked in a 1 L, 400 mM photoinitiator (PI) solution based on benzophenone (72.9 g) and tert-butylperoxybenzoate (TBPB; 76.1 mL) in ethanol (859 mL) for a period of 6 minutes. At the same time, the monomer solution was purged with nitrogen.
3. After soaking, the silicone sheets were moved to the monomer polymerization tank. This tank contained 1 L of a 350 mM solution of acrylic acid (20.6 mL) and methyl acrylate (4.5 mL) in water (975 mL). Nitrogen was purged into the tank for a period of 6 minutes.
4. After the nitrogen was turned off, UV irradiation occurred for 6 minutes.
5. This was followed by a 3-step washing process, in which silicone sheets were soaked in ethanol for 6 minutes. This was followed by subsequent soaks in a pH 3.4 HCl solution to keep the acrylic acid groups protonated and deionized water, each for 6 minutes as well.
6. Samples were hung to air dry after the washing steps.

To test the ability to regenerate the antimicrobial nature of the coat, the following steps were completed.

1. The coated device was dipped in a pH 9.5 NaOH solution for a period of 6 minutes to deprotonate the coating layer.
2. The coated device was then moved to a solution of deionized water to neutralize the base.
3. The coated device was then moved to a pH 3.4 HCl solution to re-protonate the coating.
4. The sheet was then left to air dry.
5. Steps 1 to 4 were repeated again if a second recharge cycle was desired.

Comparative Coating (I)

This first comparative coating was made as described above, however, an alternative 3-step washing process, involving a first wash in ethanol, a second wash in alkaline TRIZMA solution (10 mM; pH 9), and a third wash in deionized water, was used. Thus, this comparative coating was not protonated.

Comparative Coating (II)

1. A polystyrene-block-polyacrylic acid (PS-b-AA) block copolymer was purchased from Polymer Source (Dorval, QC) that had a composition of $M_w$ 155760-b-133340 or approximately 46% by weight acrylic acid. The latter copolymer contains an acrylic acid percentage that was similar to the acrylic acid compositions (approximately 20-40% by weight) of copolymers shown to be antimicrobial by Gratzl et al. (2014, 2015).
2. To coat the PS-b-AA on silicone sheets, the polymer was dissolved in THF (as instructed by the manufacturer), at a concentration of 0.1%.
3. A dip-and-dry approach was used to coat the silicone sheets.
4. A 65 mL solution of 0.1% PS-b-AA was made and the silicone sheets were dipped in it (under gentle agitation) for 30 minutes. This was followed by a 30 min drying step. This was repeated a total of 3 times.
5. Alternatively, to exactly replicate the conditions used by Gratzl et. al (2015), 100 mg of polymer solution were placed on a 1.8 cm×1.8 cm glass cover slide and dried in preparation for antimicrobial testing.

Contact Angle Measurements

A method of measuring contact angle was devised to give more information of about the coating surface as follows:

1. 10 μL of water was dropped onto the sample in the form of a droplet.
2. A camera, (set at the plane of the sample) took a picture of the droplet at time=0. Subsequent photos of the droplet were taken at 5 minutes and 10 minutes.

3. The image was then analyzed for contact angle by taking an angle measurement between the surface and the angle it makes with the droplet.

Abrasion Resistance

To determine the ability for the coating to stay on the surface, a qualitative abrasion test was developed as follows:

1. The sample was run under hot tap water and rubbed with a gloved hand for a period of 1 minute.
2. The contact angle for the sample was measured prior to and after the rubbing to determine if a change to the surface had occurred. Contact angle calculations were completed as set out above.

Zone of Inhibition

Antimicrobial activity against *Escherichia coli* was assessed using the Kirby-Bauer test. A zone of inhibition (ZOI) around the silicone coated pieces was used to indicate antibacterial activity as well as the ability of the antimicrobial to elute from the sample. Samples were transferred to new plates daily for up to 3 days.

The zone of inhibition was calculated as the diameter free of *E. coli* minus the diameter of the contact inhibition from the sample.

Log Reduction

The sheets were cut into 2"×2" pieces for testing. Samples and controls were cut in the same manner. There were a minimum of 3 replicates per sample per time point.

1. The test samples and controls were each exposed to UV irradiation to help sterilize the sheet.
2. Bacterial cultures (18-24 hours old) were directly diluted in Nutrient Broth (1:500) to yield a concentration of 2.5-10×$10^6$ CFU/mL, with a target of 6×$10^6$ CFU/mL.
3. All test inoculum suspensions were used within 4 hours of dilution.
4. Eight aliquots of 40 L of test inoculum were placed onto the surfaces (in triplicate) for all time points.
5. Three (3) inoculated control segments and three (3) inoculated treated segments were harvested by washing with 10 mL (10×1 mL) of sterile Dey/Engley (D/E) broth into a 50 mL centrifuge tube immediately after inoculation.
6. The centrifuge tube was then vigorously vortexed (30 s) and sonicated (30 s) to elute any viable microorganisms still attached to the surface.
7. Dilutions were plated on their corresponding growth agar (PDA, SDA or TSA). These dilutions resulted in concentrations of $10^5$, $10^4$ and $10^3$ CFU/mL.
8. Steps 5 to 7 were repeated for controls and samples that were kept in the incubator for 24 hours after exposure to the bacterial inoculum.

Results and Discussion

Contact Angle Measurements

Contact angle measurements were made using a water drop method to help determine the characteristics of the coatings. The results can be seen in Table 1 and in FIG. 1:

TABLE 1

Contact Angles of Various Coatings before and after abrasion

| Material | Contact Angle (°) Initial | Contact Angle (°) Post-abrasion |
|---|---|---|
| A. Silicone Control | 82 ± 2 | 87 ± 4 |
| B. Comparative Coating (I) | 43 ± 2 | 35 ± 2 |
| C. Non-Eluting Antimicrobial Coating | 73 ± 2 | 70 ± 5 |
| D. Non-Eluting Antimicrobial Coating (1 base wash) | 73 ± 8 | 71 ± 3 |
| E. Comparative Coating (II) | 76 ± 4 | 76 ± 5 |

The contact angle of silicone was found to be around 80°, indicating it is nearly hydrophobic, which is to be expected. When Comparative Coating (I) was applied on the surface, the contact angle dropped to 40°, which is indicative of its hydrophilic nature. The Non-Eluting Antimicrobial Coating on the other hand had a contact angle around 70°. This reflects that the surface has become protonated and there is little need for water to wet the surface. This is true even after one wash cycle with base and acid. Similarly, the Comparative Coating (II) exhibited a more hydrophobic characteristic than that of Comparative Coating (I), comparable to that of the Non-Eluting Antimicrobial Coating. Since these were specifically chosen as being coatings of a similar nature, this result was not unexpected.

Abrasion Resistance

The coatings on the silicone surfaces were assessed for resistance to abrasion by rubbing the coating under hot water and assessing contact angle afterwards. Visual inspection of Comparative Coating (II) samples indicated that most of the coating was removed by rubbing. However, there was sufficient residual material left after abrasion of Comparative Coating (II) to achieve a reduction of the contact angle relative to uncoated silicone that was not substantially different than the contact angle reduction observed with the non-abraded sample (Table 1). The contact angles of the interpenetrating covalent coatings (Comparative Coating (I) and Non-Eluting Antimicrobial Coating) did not increase nor did they produce debris after abrasion indicating that these coatings were completely abrasion-resistant.

Zone of Inhibition

When coated silicone sheets were exposed to *E. coli* in a zone of inhibition test, no visible growth inhibition occurred outside of the regions making contact with the sample. The absence of a growth inhibition zone outside of the contact regions indicates that the coatings do not elute antimicrobial substances and supports the notion that any antimicrobial activity observed with use of the coated materials is a result of the contact-killing ability of the polymers themselves.

Log Reduction

Figure 2:
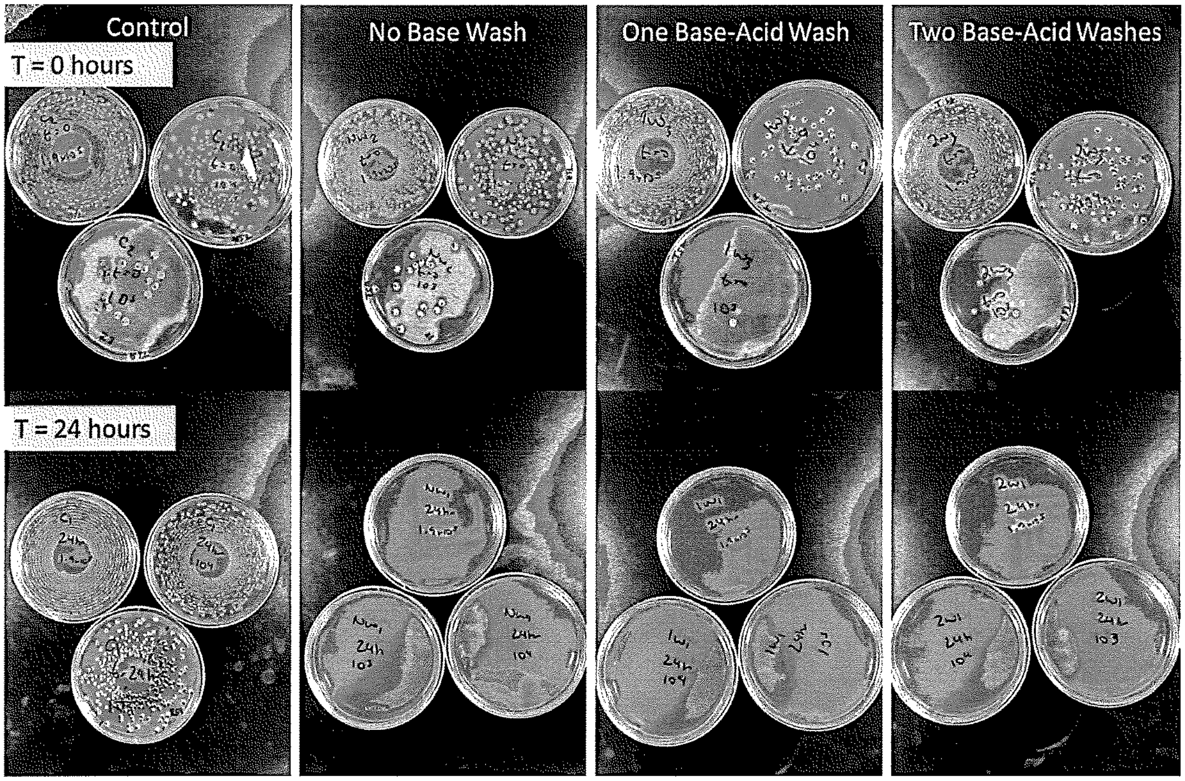
FIG. 2 shows the log reduction over 24 hours of the Non-Eluting Antimicrobial Coating (with various wash states).

A log reduction study was conducted using the silicone coated materials over the course of 24 hours. The visual results can be seen in FIG. 2 and Table 2.

TABLE 2

Log Reduction vs. *E. coli*

| Material | 24 hour log reduction |
|---|---|
| Comparative Coating (I) | −1.16 ± 0.02 |
| Non-Eluting Antimicrobial Coating | 5.90 ± 0.04 |
| Non-Eluting Antimicrobial Coating (1 base wash) | 5.28 ± 0.02 |

TABLE 2-continued

| Log Reduction vs. *E. coli* | |
|---|---|
| Material | 24 hour log reduction |
| Non-Eluting Antimicrobial Coating (2 base wash) | 5.41 ± 0.02 |
| Comparative Coating (II) | −0.79 ± 0.17 |

When *E. coli* was exposed to the coated samples, no bacteria survived as predicted. However, the Comparative Coating (II) control sample resulted in growth on the sample, akin to the controls. The latter result is contrary to expectations based on the results of Gratzl et al. (2014, 2015) in which a polymer of similar composition was substantially antimicrobial. The lack of antimicrobial effect of the PS-PAA polymer observed in the comparative study is likely due to slight differences in the molecular weight and acrylic acid content relative to the PS-PAA polymers used in Gratzl et al. (2014, 2015), which serves to emphasize the robustness of the interpenetrating covalent grafting approach described herein.

Summary

The Non-Eluting Antimicrobial Coating tested in these experiments is superior to the Comparative Coatings (I) and (II). This is especially true for abrasion resistance and log reduction.

Example 4—Further Antimicrobial Testing of the Non-Eluting Antimicrobial Coating Silicone sheets were tested according to a Protocol for Modified ISO 22196 (a modification of the International Standard ISO 22196 Plastics—Measurement of Antibacterial Activity on Plastics Surfaces). The protocol was used to assess the antimicrobial activity against two challenge organisms.

More specifically, the following lots of silicone sheets were tested according to Protocol for Modified ISO 22196:

1. Uncoated (control)
2. Comparative Coating (I) from Example 3
3. Non-Eluting Antimicrobial Coating from Example 3

The test articles were inoculated with the following challenge organisms:

1. *Candida albicans* ATCC 10231
2. *Pseudomonas aeruginosa* ATCC 9027
3. *Enterococcus faecalis* (VRE) ATCC 51299

The inoculated test articles were incubated at 30° C.±1.0° C. Immediately (0 hours of incubation) and after 24 hours±1 hour, the surviving microbes were harvested from the test material and enumerated via plate counts. The test was performed in triplicate and according to GLP.

The Antimicrobial Activity (R-values) of challenge organisms were calculated according to the following calculation:

$$R=(A_0)-(A_t)$$

Where R is the value of antibacterial activity; $A_0$ is the average of the common logarithm of the number of viable bacteria, in CFU/Coupon, recovered from treated test coupons immediately after inoculation. At is the average of the common logarithm of the number of viable bacteria, in CFU/Coupon, recovered from treated test specimens after each contact time (24±1 hours).

The results indicate that only protonated coatings are significantly antimicrobial (Table 3) achieving a reduction of the inoculum of 3-log or greater.

TABLE 3

| | Viable Organism Reduction ($Log_{10}$) | | |
|---|---|---|---|
| Microorganism | Silicone Control | CovaCoat (unprotonated) | CovaCoat (protonated) |
| *Pseudomonas aeruginosa* | −1.89 | −2.25 | >4.53 |
| *Enterococcus faecalis* | 0.34 | 0.11 | 3.00 |
| *Escherichia coli* | −1.24 | 0.66 | 6.05 |

Example 5—Thrombogenicity Test Results

An assessment of the ability of protonated coatings to resist thrombus formation was undertaken using an in vitro model of recirculated bovine blood. Test samples consisted of uncoated 8 Fr polyurethane tubing (control), the same tubing with Comparative Coating (I) from Example 3 and polyurethane tubing coated with the non-eluting antimicrobial coating from Example 3.

Fresh heparinized bovine blood with autologous $^{111}$In-labeled platelets was divided into 6 portions. The blood was recirculated in tubing segments in which the polyurethane test samples were deployed after rinsing with saline in situ for 30 seconds. At the end of the experiment, the samples were explanted from the tubing, rinsed with saline, photographed, and placed in a gamma counter for thrombus quantification. 1 cm at the distal tip and 2 cm at the insertion point of the catheter were excluded from the quantification due to the presence of a sealant at the distal tip and flow disturbance at the insertion site, which may have variably influenced thrombosis at those locations.

Figure 3:
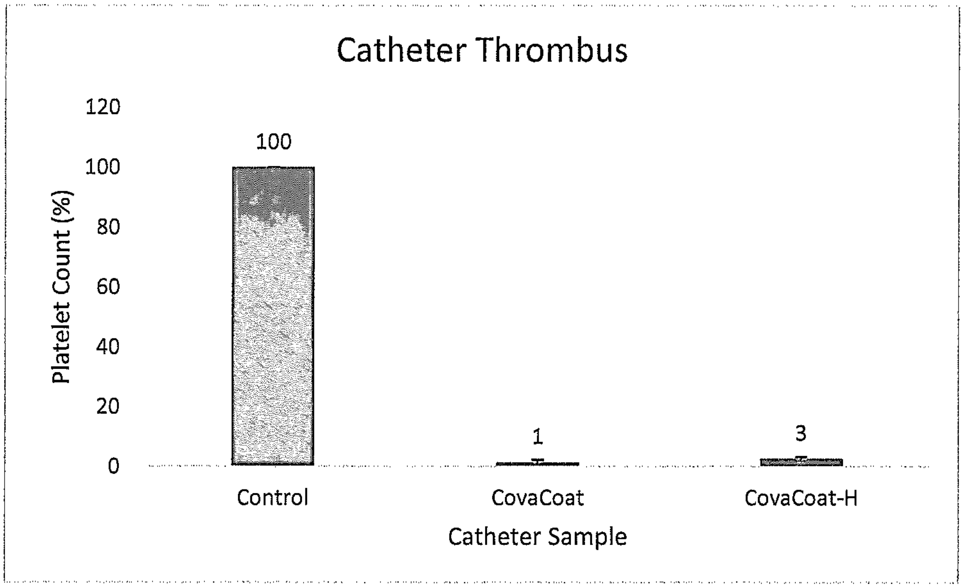
FIG. 3 shows the ability of the Non-Eluting Antimicrobial Coating (CovaCoat-H) to reduce thrombus formation relative to uncoated material in an in vitro blood loop study.

Radiation data was collected from each sample and was reflective of the amount of thrombus present on each catheter since platelets play a major role in the blood coagulation cascade. Since the uptake of the radioactive label by platelets varies from experiment to experiment, the results were normalized for each of the six replicate runs per sample with respect to the total number of radioactive platelets associated with the uncoated control. As demonstrated in FIG. 3, both Comparative Coating (I) and the Non-Eluting Antimicrobial Coating drastically reduced thrombus formation relative to the control sample. The latter coating achieved a 97% reduction in the amount of thrombus.

Example 6—Analysis of Foley Catheter Balloons Coated with Acrylic Acid or Acrylic Acid/Methyl Acrylate Introduction The composition of monomers used for coating Foley catheters plays an important role on the properties of the coating. The purpose of this study was to determine the difference in the coating, particularly in the balloon region of the catheter, between a 350 mM acrylic acid coating composition and a 350 mM acrylic acid/methyl acrylate (6:1) coating composition.

Materials and Methods

Samples Tested

Foley catheters, 12 French (lot 20141225)

Materials Preparation

Preparation of Photo-Initiator (PI) Solution (400 mM)

Benzophenone (72.89 g) was dissolved in EtOH (860 mL). Once fully dissolved, tert-butylperoxybenzoate (76 mL) was added. The mixture was stirred for 10 minutes before use.

Preparation of Monomer Solution

Acrylic acid monomer solution was prepared by adding acrylic acid (AA) (48 mL) to deionized (DI) water (1950 mL). The solution was stirred for 10 minutes before use.

Acrylic acid/methyl acrylate solution monomer solution was prepared by adding AA (41 mL) and methyl acrylate (MA) (9 mL) to DI water (1950 mL). The solution was stirred for 10 minutes before use.

Coating Process 1. 10 Foley catheters were submerged in 400 mM PI solution for 6 minutes. The catheters were then removed from the PI solution and shaken in air for 30 seconds to remove excess PI solution.
2. The catheters were placed into a polymerization tank containing 2 L of desired monomer solution.
3. The system was purged with nitrogen gas for 6 minutes. After 6 minutes, nitrogen bubbling was stopped and any gas bubbles were then removed by shaking catheters in monomer solution.
4. UV irradiation was applied for 6 minutes.
5. The UV irradiation was stopped. Catheters were removed from the polymerization tank and washed with EtOH (6 minutes), followed by 50 mM Trizma Base solution (DK-084-181, 6 minutes), followed by DI water (6 minutes)
6. Five catheters were stained using a 0.1% (w/v) methylene blue solution. Five catheters were left unstained.
7. Catheters were hung to dry in air overnight.

Balloon Analysis

1. Catheters were placed in a 60° C. oven for 30 minutes.
2. A 30 ml syringe filled with 30 cc of air was attached to the catheter.
3. Air was pushed to fill the balloon. At 1.5, 2.0, 3.0 and 30 cc, the balloon was assessed and a photo was taken.
4. Balloon failure test
5. Catheters were placed in a 60° C. oven for 30 minutes.
6. Catheters were attached to a 60 ml syringe filled with 60 cc of air.
7. The air was pushed into the balloon. 60 cc of air was held in the balloon before being released. A balloon failure was recorded if the balloon was broken at any volume up to 60 cc.

Balloon Failure Test

1. Catheters were placed in a 60° C. oven for 30 minutes.
2. Catheters were attached to a 60 ml syringe filled with 60 cc of air.
3. The air was pushed into the balloon. 60 cc of air was held in the balloon before being released. A balloon failure was recorded if the balloon was broken at any volume up to 60 cc.

Results and Discussion

Coating Procedure

No significant difference was observed for coating with AA or AA/MA. Both monomer compositions were found to produce a consistent coating on the inside and outside of the catheter, as indicated by methylene blue staining.

Balloon Analysis

Figure 4:
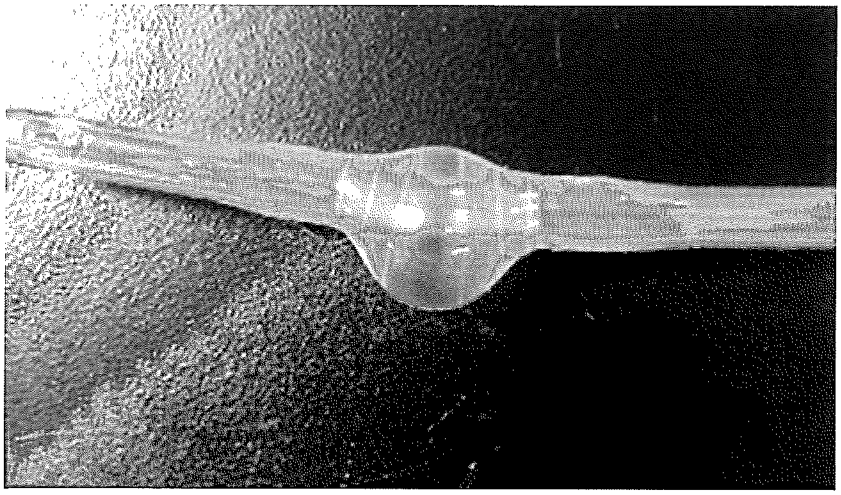
FIG. 4 shows the results of a balloon analysis, where balloons were uncoated (4A), coated with an AA/MA (6:1) coating (4B), or coated with an AA coating (4C) and filled with 1.5 cc air.
Figure 4:
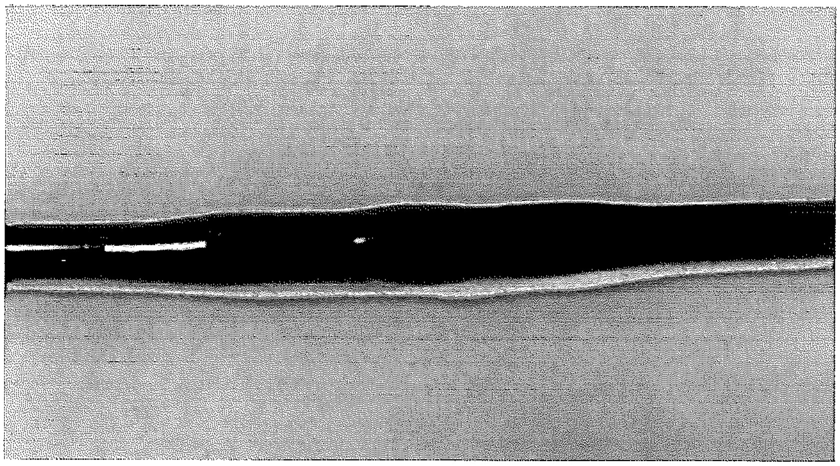
Figure 4:
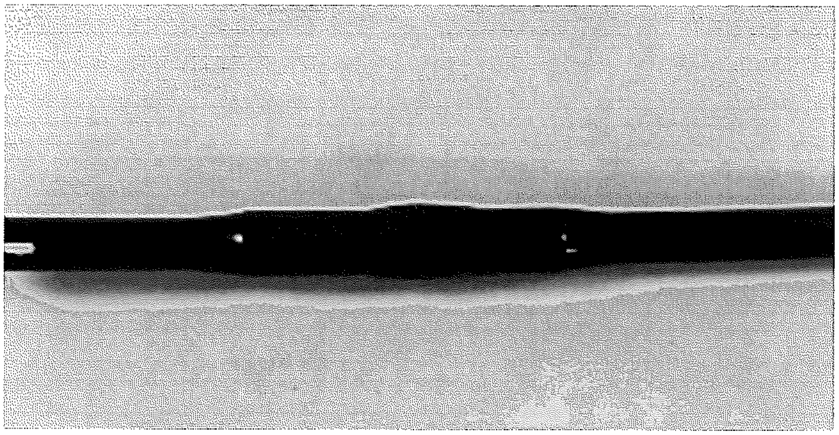
Figure 5:
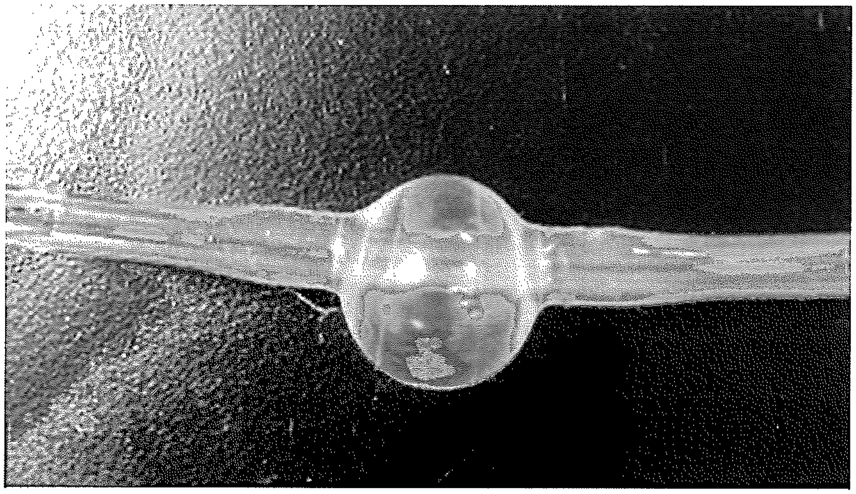
FIG. 5 shows the results of a balloon analysis, where balloons were uncoated (5A), coated with an AA/MA (6:1) coating (5B), or coated with an AA coating (5C) and filled with 2 cc air.
Figure 5:
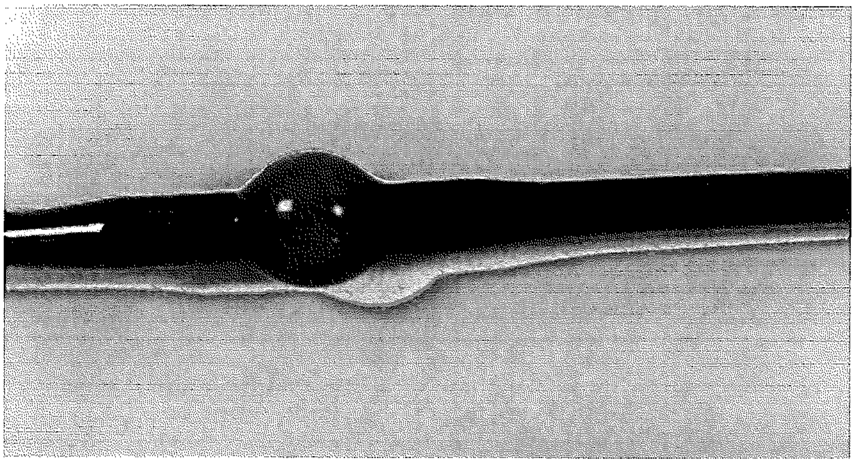
Figure 5:
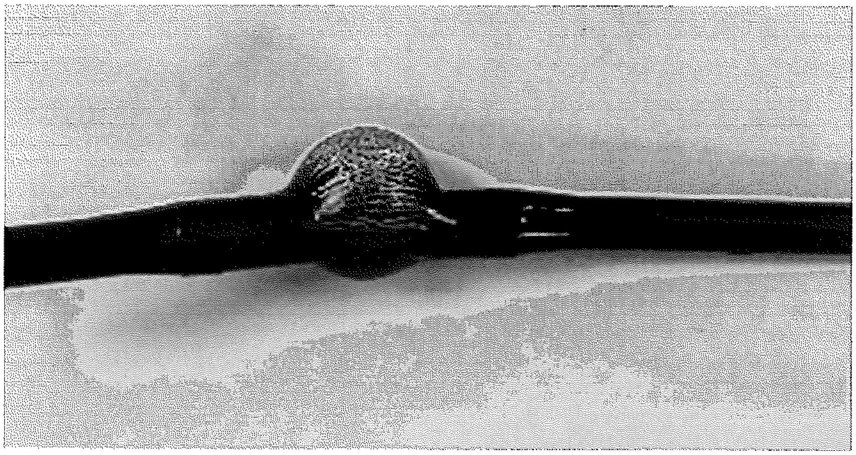
Figure 6:
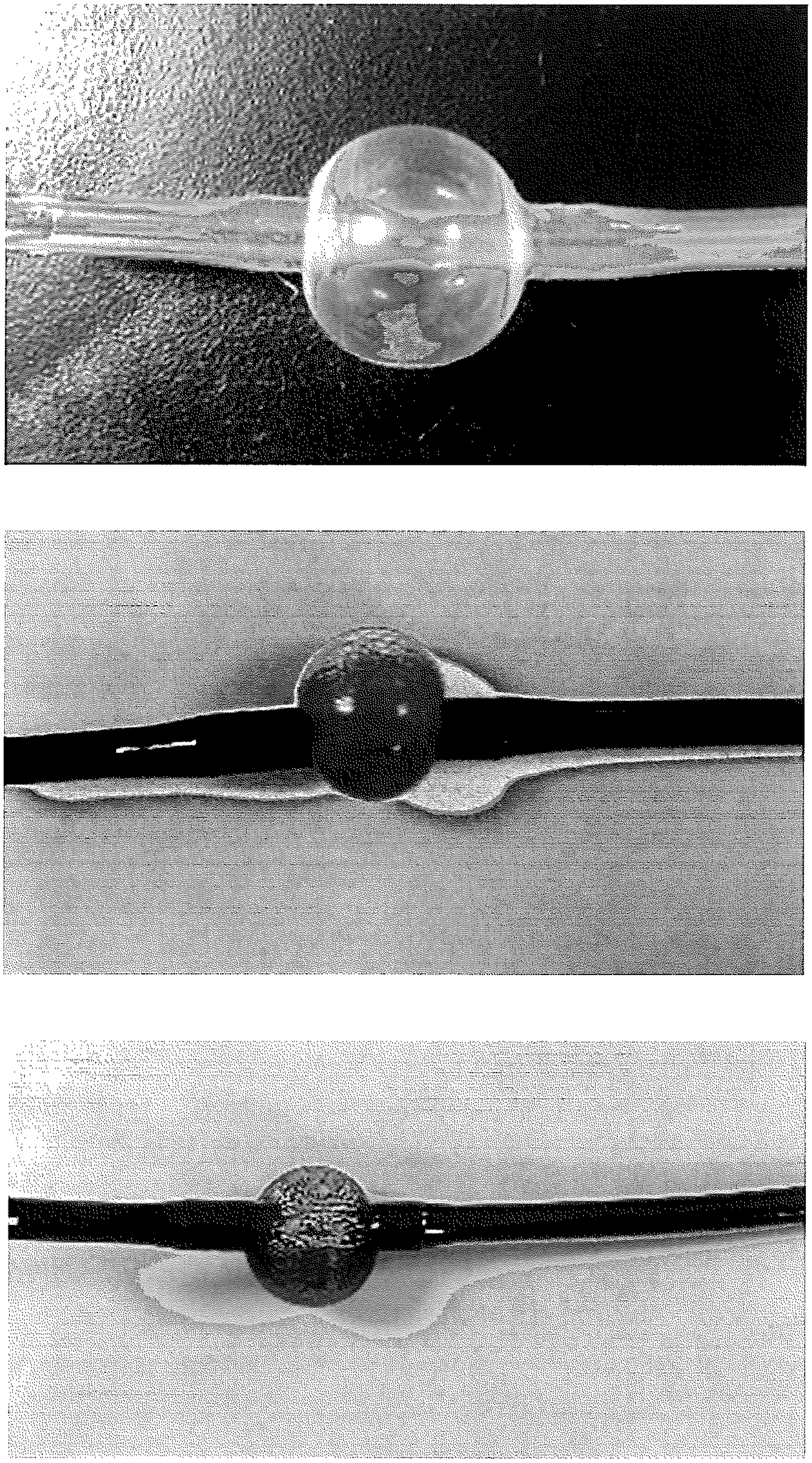
FIG. 6 shows the results of a balloon analysis, where balloons were uncoated (6A), coated with an AA/MA (6:1) coating (6B), or coated with an AA coating (6C) and filled with 3 cc air.
Figure 7:
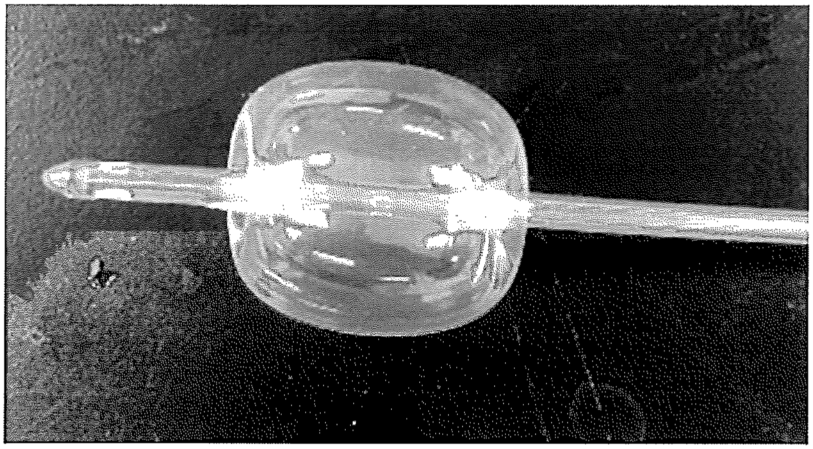
FIG. 7 shows the results of a balloon analysis, where balloons were uncoated (7A), coated with an AA/MA (6:1) coating (7B), or coated with an AA coating (7C) and filled with 30 cc air.
Figure 7:
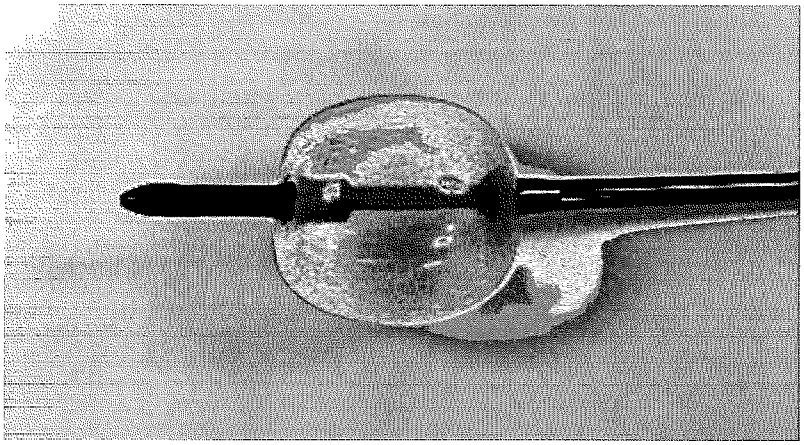
Figure 7:
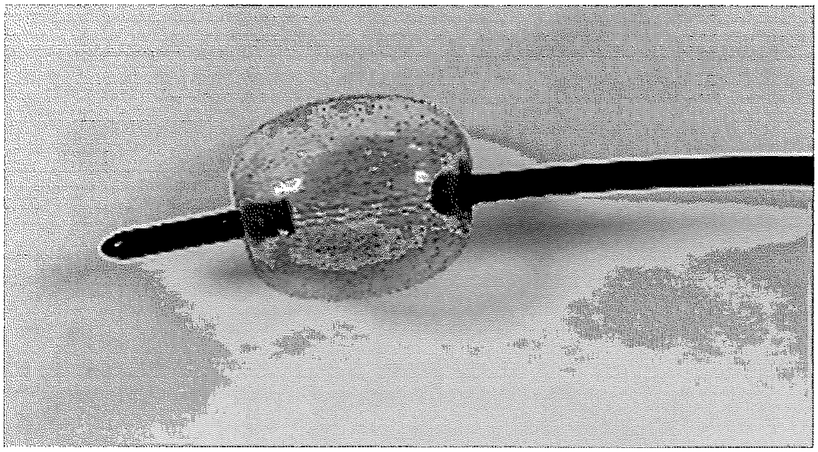

The balloons were analyzed for their relative amount of cracking, as determined by the relative dyed area when the balloon was filled with air. Estimations for the amount of area that contained dye when filled with 30 cc of air were made. The scale used was from 0-1, where 0 is no blue dye (uncoated control) and 1 is fully covered in methylene blue dye. Therefore, a higher number represents a lower degree of cracking. It was found that the AA coating had significantly less methylene blue dyed area when filled with 30 cc air than the AA/MA coating, indicating the AA coating had significantly more cracking (Table 4; FIGS. 4-7, where FIGS. 4A, 4B, and 4C show 1.5 cc air for control, AA/MA, and AA, respectively; FIGS. 5A, 5B, and 5C show 2 cc air for control, AA/MA, and AA, respectively; FIGS. 6A, 6B, and 6C show 3 cc air for control, AA/MA, and AA, respectively; and FIGS. 7A, 7B, and 7C show 30 cc air for control, AA/MA, and AA, respectively).

TABLE 4

Methylene blue staining analysis with 30 cc air

| Sample | Coating | Area dyed |
|---|---|---|
| 78-2 | AA/MA (6:1) | 0.5 |
| 78-3 | | 0.5 |
| 78-4 | | 0.4 |
| 79-2 | AA | 0.3 |
| 79-3 | | 0.2 |
| 79-4 | | 0.2 |

Balloon Failure Test

The balloons were slowly filled with 60 cc of air. If the balloon burst, the syringe position was noted at point of break. If the balloons did not break at 60 cc of air added, the air was held for 10 seconds. It was found that none of the uncoated controls had broken balloons. The AA/MA coating had similar results, with no balloons breaking after 60 cc of air for 10 seconds. All three of the tested AA coatings resulted in broken balloons; two before being fully filled and the third breaking while holding the 60 cc for 10 seconds (Table 5).

TABLE 5

Balloon failure test results

| Sample | Coating | Pass or Fail | Fail point |
|---|---|---|---|
| Control 1 | N/A | Pass | N/A |
| Control 2 | | Pass | |
| Control 3 | | Pass | |
| 78-2 | AA/MA (6:1) | Pass | N/A |
| 78-3 | | Pass | |
| 78-6 | | Pass | |
| 79-2 | AA | Fail | 56 cc |
| 79-3 | | Fail | 55 cc |
| 79-6 | | Fail | 60 cc |

Thus, Foley 12 French catheters were coating using either 350 mM AA or 350 mM 6:1 AA:MA. It was found that AA resulted in a more rigid coating that was more prone to cracking and had a balloon that broke more easily. The AA/MA coating had noticeably less cracking and had no balloons that broke under the tested conditions.

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

The invention claimed is:

1. A method of coating a surface of a device, the method comprising:

- applying at least one water soluble vinyl carboxylic acid monomer to the device;
- applying at least one water soluble neutral monomer to the device, wherein the at least one water soluble neutral monomer has a glass transition temperature of less than about 100° C. in homopolymeric form;
- graft-polymerizing a copolymer comprising the at least one vinyl carboxylic acid monomer and the at least one neutral monomer onto the device; and protonating the vinyl carboxylic acid monomer in the graft-polymerized copolymer.

2. The method of claim 1, wherein the vinyl carboxylic acid monomer is selected from the group consisting of acrylic acid, 2-bromoacrylic acid, 2-(bromomethyl) acrylic acid, 2-carboxyethyl acrylate, 2-ethylacrylic acid, itaconic acid, methacrylic acid, 2-propylacrylic acid, sodium acrylate, sodium methacrylate, 2-(trifluoromethyl) acrylic acid, 4-vinylbenzoic acid, and combinations thereof and wherein the neutral monomer is selected from the group consisting of acrylates, methacrylates, acrylamides, methacrylamides, vinyl compounds, and combinations thereof.

3. The method of claim 1, further comprising ionizing the coating after the polymerizing step, wherein ionizing the coating comprises applying a basic solution to the coating, wherein the basic solution is selected from the group consisting of TRIZMA base, disodium tetraborate, sodium carbonate, and hydroxides such as ammonium hydroxide, calcium hydroxide, sodium hydroxide, and mixtures thereof.

4. The method of claim 3, further comprising applying an antimicrobial agent comprising silver ions to the coating after the step of ionizing the coating.

5. The method of claim 4, wherein the method further comprises applying a photostabilizer comprising brilliant green and/or pyrrolidone carboxylic acid to the device.

6. The method of claim 5, wherein the device is soaked in a solution comprising the photostabilizer, pyrrolidone carboxylic acid, and silver ions.

7. The method of claim 4, wherein the method further comprises washing the device in a basic solution after the step of applying the antimicrobial agent.

8. The method of claim 1, wherein the protonating comprises applying an acidic solution to the coating, wherein the acidic solution comprises an acid selected from the group consisting of HCl, HBr, HI, $HClO_4$, $H_2SO_4$, $HNO_3$, sodium hydrogen sulfate, sulfonic acid, acetic acid, phosphoric acid, phosphorous acid, sulfurous acid, trichloroacetic acid, salicylic acid, phthalic acid, nitrous acid, lactic acid, hydroiodic acid, formic acid, citric acid, tartaric acid, and combinations thereof.

9. The method of claim 1, further comprising a preliminary step of applying an initiator solution to the device, wherein the initiator solution is a photoinitiator solution, wherein the photoinitiator solution comprises a photoinitiator selected from the group consisting of peresters, a-hydroxyketones, benzil ketals, benzoins and their derivatives and mixtures thereof, such as tert-butylperbenzoate and/or benzophenone.

10. The method of claim 1, wherein the polymerizing step comprises applying UV light to the device and, optionally, bubbling an inert gas such as nitrogen through the monomers, before and/or during the step of applying UV light to the device.

11. The method of claim 1, wherein the vinyl carboxylic acid monomers and the neutral monomers are present in the same solution.

12. The method of claim 1, wherein the coating comprises at least one of the following characteristics:

- is inherently antimicrobial, optionally showing a greater than about 2-log reduction in microbes within about 24 hours, such as a greater than about 2-log, 3-log, 4-log, or 5-log reduction in microbes within about 5 minutes, 30 minutes, 1 hour, 2 hours, 6 hours, 12 hours, 18 hours, or 24 hours;
- is inherently antithrombogenic, optionally showing a greater than about 80% reduction, such as a greater than about 85%, 90%, 95%, 96%, 97%, 98%, or 99% reduction, relative to an uncoated surface;
- releases low or no particulates, optionally releasing fewer particulates than an uncoated surface;
- is lubricious;
- has high resistance to cracking when expanded or inflated;
- has high resistance to delamination as demonstrated by the maintenance of hydrophilicity after exposure to high shear force.

13. The method of claim 1, wherein exposure of the polymeric coating to an altered pH environment restores its inherent biological activity, such as antimicrobial activity, antithrombogenicity, low to no particulate release, lubricity, resistance to cracking, and/or maintenance of hydrophilicity.

* * * * *